United States Patent [19]
Haupt et al.

[11] Patent Number: 5,831,002
[45] Date of Patent: Nov. 3, 1998

[54] ANTITUMOR PEPTIDES

[75] Inventors: Andreas Haupt; Franz Emling, both of Ludwigshafen, Germany; Cynthia Romerdahl, Wayland, Mass.

[73] Assignee: BASF Aktiengesellschaft, Germany

[21] Appl. No.: 472,453

[22] Filed: Jun. 7, 1995

Related U.S. Application Data

[63] Continuation-in-part of Ser. No. 431,795, May 1, 1995, abandoned, which is a continuation of Ser. No. 985,696, Nov. 25, 1992, abandoned, which is a continuation-in-part of Ser. No. 885,788, May 20, 1992, abandoned.

[51] Int. Cl.$^6$ .................................................. A61K 38/08
[52] U.S. Cl. ........................ 530/329; 530/330; 514/16; 514/17; 514/18
[58] Field of Search .................. 514/16–18; 530/329, 530/330

[56] References Cited

U.S. PATENT DOCUMENTS

| | | | |
|---|---|---|---|
| 4,816,444 | 3/1989 | Pettit et al. | 514/17 |
| 5,504,191 | 4/1996 | Pettit et al. | 530/330 |
| 5,530,097 | 6/1996 | Pettit et al. | 530/330 |

FOREIGN PATENT DOCUMENTS

| | | |
|---|---|---|
| 0 398 558 | 11/1990 | European Pat. Off. . |
| 0 598 129 | 5/1994 | European Pat. Off. . |
| 93/23424 | 11/1993 | WIPO . |

OTHER PUBLICATIONS

Pettit, G.R. et al., "Isolation of Dolastatins 10–15 From the Marine Mollusc *Dolabella Auricularia*," Tetrahedron 49(41) : 9151–9170 (1993).

Pettit, G.R. et al., The Dolastatins 20. A Convenient Synthetic Route to Dolastatin 15, Tetrahedron, 50(42) : 12097–12108 (1994).

Pettit, G.R. et al., "The Isolation and Structure of a Remarkable Marine Animal Antineoplastic Constituent: Dolastatin 10", *J. Am. Chem. Soc.* 109: 6883–6885 (1987).

Pettit, G.R. et al., "Isolation and Structure of the Cytostatic Linear Depsipetide Dolastatin 15", *J. Org. Chem.*, 54: 6005–6006 (1989).

Pettit, G.R. et al., "Isolation and Structure of the Cytostatic Depsipeptide Dolastatin 13 from the Sea Hare *Dolabella auricularia*", *J. Am. Chem. Soc.*, 111(13) : 5015–5017 (1989).

Pettit, G.R. et al., "Antineoplastic Agents. 220. Synthesis of Natural (−) –Dolastatin 15", *J. Am. Chem. Soc.*, 113: 6692–6693 (1991).

Bai, R., et al., "Dolastatin 15, a potent antimitotic depsipeptide derived from *Dolabella auricularia*. Interaction with tubulin and effects on cellcular microtubules", 1–*Pharmacology* Abstract 117: 103735g pg. 41 (1992).

Bai, R., et al., "Structure–Activity Studies with Chiral Isomers and with Segments of the Antimitotic Marine Peptide Dolastatin 10", *Biochemical Pharmacology*, 40(8) : 1859–1864 (1990).

*Primary Examiner*—Cecilia J. Tsang
*Assistant Examiner*—David Lukton
*Attorney, Agent, or Firm*—Hamilton, Brook, Smith & Reynolds, P.C.

[57] ABSTRACT

Novel compounds of the formula $$R^1R^2N\text{—CHX-CO-A-B-D-(E)}_s\text{-(F)}_t\text{-(G)}_u\text{-K} \qquad I$$

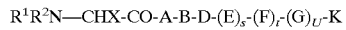

in which $R^1$, $R^2$, A, B, D, E, F, G, K, X, s, t, and u have the meanings stated in the description, and the preparation thereof are described. The novel substances have an antineoplastic effect.

10 Claims, 1 Drawing Sheet

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
( A ) LENGTH: 7 amino acids
( B ) TYPE: amino acid (C) STRANDEDNESS:
(D) TOPOLOGY: linear (ii) MOLECULE TYPE: peptide (xi) SEQUENCE DESCRIPTION: SEQ ID NO:1:

Xaa Val Xaa Pro Pro Val Phe
1               5

(2) INFORMATION FOR SEQ ID NO:2:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:2:

Xaa Val Xaa Pro Xaa
1               5

(2) INFORMATION FOR SEQ ID NO:3:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:3:

Xaa Val Xaa Pro Pro Val Xaa
1               5

(2) INFORMATION FOR SEQ ID NO:4:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:4:

Xaa Val Xaa Pro Pro Val His
1               5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:5:

Xaa Xaa Xaa Pro Pro Val Trp
1               5

(2) INFORMATION FOR SEQ ID NO:6:

(i) SEQUENCE CHARACTERISTICS:
(A) LENGTH: 7 amino acids
(B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:6:

Xaa Val Xaa Pro Pro Xaa Phe
1               5

( 2 ) INFORMATION FOR SEQ ID NO:7:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:7:

Xaa Val Xaa Pro Pro Ile Phe
1               5

( 2 ) INFORMATION FOR SEQ ID NO:8:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:8:

Xaa Val Xaa Pro Xaa Val Phe
1               5

( 2 ) INFORMATION FOR SEQ ID NO:9:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:9:

Xaa Val Xaa Xaa Pro Val Phe
1               5

( 2 ) INFORMATION FOR SEQ ID NO:10:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:10:

Xaa Val Xaa Pro Pro Val Phe
1               5

( 2 ) INFORMATION FOR SEQ ID NO:11:

( i ) SEQUENCE CHARACTERISTICS:
( A ) LENGTH: 6 amino acids
( B ) TYPE: amino acid (C) STRANDEDNESS:
        (D) TOPOLOGY: linear (i i) MOLECULE TYPE: peptide (x i) SEQUENCE DESCRIPTION: SEQ ID NO:11:

Xaa  Xaa  Pro  Pro  Val  Phe
    1                        5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:12:

Xaa  Ile  Xaa  Pro  Pro  Val  Phe
    1                   5

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:13:

Xaa  Xaa  Xaa  Pro  Pro  Val  Phe
    1                   5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:14:

Xaa  Leu  Xaa  Pro  Pro  Val  Phe
    1                   5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:15:

Xaa  Val  Xaa  Pro  Pro  Phe  Phe
    1                   5

(2) INFORMATION FOR SEQ ID NO:16:

(i) SEQUENCE CHARACTERISTICS:
        (A) LENGTH: 6 amino acids
        (B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:16:

Xaa  Val  Xaa  Pro  Pro  Val
1                    5

( 2 ) INFORMATION FOR SEQ ID NO:17:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:17:

Xaa  Val  Xaa  Pro  Pro  Xaa
1                    5

( 2 ) INFORMATION FOR SEQ ID NO:18:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:18:

Xaa  Val  Xaa  Pro  Pro  Val
1                    5

( 2 ) INFORMATION FOR SEQ ID NO:19:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:19:

Xaa  Xaa  Xaa  Pro  Pro  Val
1                    5

( 2 ) INFORMATION FOR SEQ ID NO:20:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:20:

Xaa  Val  Xaa  Xaa  Pro  Val
1                    5

( 2 ) INFORMATION FOR SEQ ID NO:21:

( i ) SEQUENCE CHARACTERISTICS:
( A ) LENGTH: 6 amino acids
( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:21:

Xaa  Val  Xaa  Pro  Xaa  Val
1                   5

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:22:

Xaa  Val  Xaa  Xaa
1

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:23:

Xaa  Xaa  Xaa  Pro  Pro
1                   5

( 2 ) INFORMATION FOR SEQ ID NO:24:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:24:

Xaa  Xaa  Pro  Pro
1

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:25:

Xaa  Val  Xaa  Pro
1

( 2 ) INFORMATION FOR SEQ ID NO:26:

( i ) SEQUENCE CHARACTERISTICS:
        ( A ) LENGTH: 5 amino acids
        ( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:26:

Xaa Xaa Xaa Pro Xaa
1               5

( 2 ) INFORMATION FOR SEQ ID NO:27:

( i ) SEQUENCE CHARACTERISTICS:
( A ) LENGTH: 5 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:27:

Xaa Xaa Pro Pro Val
1               5

( 2 ) INFORMATION FOR SEQ ID NO:28:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:28:

Xaa Val Pro Pro Val Phe
1               5

( 2 ) INFORMATION FOR SEQ ID NO:29:

( i ) SEQUENCE CHARACTERISTICS:
( A ) LENGTH: 4 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:29:

Xaa Val Pro Pro
1

( 2 ) INFORMATION FOR SEQ ID NO:30:

( i ) SEQUENCE CHARACTERISTICS:
( A ) LENGTH: 4 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:30:

Xaa Xaa Pro Xaa
1

( 2 ) INFORMATION FOR SEQ ID NO:31:

( i ) SEQUENCE CHARACTERISTICS:
( A ) LENGTH: 6 amino acids
( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:31:

Xaa Val Xaa Pro Xaa Phe
1               5

( 2 ) INFORMATION FOR SEQ ID NO:32:

( i ) SEQUENCE CHARACTERISTICS:
( A ) LENGTH: 5 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:32:

Xaa Xaa Pro Pro Xaa
1               5

( 2 ) INFORMATION FOR SEQ ID NO:33:

( i ) SEQUENCE CHARACTERISTICS:
( A ) LENGTH: 5 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:33:

Xaa Xaa Pro Xaa Phe
1               5

( 2 ) INFORMATION FOR SEQ ID NO:34:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:34:

Xaa Val Xaa Pro Pro Phe Phe
1               5

( 2 ) INFORMATION FOR SEQ ID NO:35:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:35:

Xaa Val Xaa Pro Pro Xaa Xaa
1               5

( 2 ) INFORMATION FOR SEQ ID NO:36:

( i ) SEQUENCE CHARACTERISTICS:
( A ) LENGTH: 7 amino acids
( B ) TYPE: amino acid ( C ) STRANDEDNESS:
           ( D ) TOPOLOGY: linear ( i i ) MOLECULE TYPE: peptide ( x i ) SEQUENCE DESCRIPTION: SEQ ID NO:36:

Xaa  Val  Xaa  Pro  Pro  Leu  Phe
     1                      5

( 2 ) INFORMATION FOR SEQ ID NO:37:

( i ) SEQUENCE CHARACTERISTICS:
           ( A ) LENGTH: 7 amino acids
           ( B ) TYPE: amino acid
           ( C ) STRANDEDNESS:
           ( D ) TOPOLOGY: linear ( i i ) MOLECULE TYPE: peptide ( x i ) SEQUENCE DESCRIPTION: SEQ ID NO:37:

Xaa  Val  Xaa  Pro  Pro  Ile  Phe
     1                      5

( 2 ) INFORMATION FOR SEQ ID NO:38:

( i ) SEQUENCE CHARACTERISTICS:
           ( A ) LENGTH: 7 amino acids
           ( B ) TYPE: amino acid
           ( C ) STRANDEDNESS:
           ( D ) TOPOLOGY: linear ( i i ) MOLECULE TYPE: peptide ( x i ) SEQUENCE DESCRIPTION: SEQ ID NO:38:

Xaa  Val  Xaa  Pro  Pro  Val  Ala
     1                      5

( 2 ) INFORMATION FOR SEQ ID NO:39:

( i ) SEQUENCE CHARACTERISTICS:
           ( A ) LENGTH: 7 amino acids
           ( B ) TYPE: amino acid
           ( C ) STRANDEDNESS:
           ( D ) TOPOLOGY: linear ( i i ) MOLECULE TYPE: peptide ( x i ) SEQUENCE DESCRIPTION: SEQ ID NO:39:

Xaa  Xaa  Xaa  Pro  Pro  Val  Phe
     1                      5

( 2 ) INFORMATION FOR SEQ ID NO:40:

( i ) SEQUENCE CHARACTERISTICS:
           ( A ) LENGTH: 6 amino acids
           ( B ) TYPE: amino acid
           ( C ) STRANDEDNESS:
           ( D ) TOPOLOGY: linear ( i i ) MOLECULE TYPE: peptide ( x i ) SEQUENCE DESCRIPTION: SEQ ID NO:40:

Xaa  Xaa  Xaa  Pro  Pro  Val
     1                      5

( 2 ) INFORMATION FOR SEQ ID NO:41:

( i ) SEQUENCE CHARACTERISTICS:
           ( A ) LENGTH: 7 amino acids
           ( B ) TYPE: amino acid (C) STRANDEDNESS:
(D) TOPOLOGY: linear (ii) MOLECULE TYPE: peptide (xi) SEQUENCE DESCRIPTION: SEQ ID NO:41:

```
Xaa  Val  Xaa  Pro  Pro  Val  Phe
1                 5
```

(2) INFORMATION FOR SEQ ID NO:42:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:42:

```
Xaa  Val  Xaa  Pro  Pro  Val
1                 5
```

(2) INFORMATION FOR SEQ ID NO:43:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:43:

```
Xaa  Ile  Xaa  Pro  Xaa
1                 5
```

(2) INFORMATION FOR SEQ ID NO:44:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:44:

```
Xaa  Val  Xaa  Pro  Xaa  Val
1                 5
```

(2) INFORMATION FOR SEQ ID NO:45:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:45:

```
Xaa  Val  Xaa  Pro  Xaa  Leu  Phe
1                 5
```

(2) INFORMATION FOR SEQ ID NO:46:

(i) SEQUENCE CHARACTERISTICS:
(A) LENGTH: 6 amino acids
(B) TYPE: amino acid (C) STRANDEDNESS:
(D) TOPOLOGY: linear (i i) MOLECULE TYPE: peptide (x i) SEQUENCE DESCRIPTION: SEQ ID NO:46:

Xaa Val Xaa Pro Xaa Xaa
1               5

(2) INFORMATION FOR SEQ ID NO:47:

(i) SEQUENCE CHARACTERISTICS:
(A) LENGTH: 6 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:47:

Xaa Leu Xaa Pro Pro Xaa
1               5

(2) INFORMATION FOR SEQ ID NO:48:

(i) SEQUENCE CHARACTERISTICS:
(A) LENGTH: 6 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:48:

Xaa Leu Xaa Pro Pro Xaa
1               5

(2) INFORMATION FOR SEQ ID NO:49:

(i) SEQUENCE CHARACTERISTICS:
(A) LENGTH: 7 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:49:

Xaa Lys Xaa Pro Pro Val Phe
1               5

(2) INFORMATION FOR SEQ ID NO:50:

(i) SEQUENCE CHARACTERISTICS:
(A) LENGTH: 6 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:50:

Xaa Lys Xaa Pro Pro Val
1               5

(2) INFORMATION FOR SEQ ID NO:51:

(i) SEQUENCE CHARACTERISTICS:
(A) LENGTH: 5 amino acids
(B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:51:

Xaa Lys Xaa Pro Pro
1               5

( 2 ) INFORMATION FOR SEQ ID NO:52:

( i ) SEQUENCE CHARACTERISTICS:
( A ) LENGTH: 5 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:52:

Xaa Lys Xaa Pro Xaa
1               5

( 2 ) INFORMATION FOR SEQ ID NO:53:

( i ) SEQUENCE CHARACTERISTICS:
( A ) LENGTH: 6 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:53:

Xaa Xaa Xaa Pro Pro Val
1               5

( 2 ) INFORMATION FOR SEQ ID NO:54:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:54:

Xaa Xaa Xaa Pro Pro Val Phe
1               5

( 2 ) INFORMATION FOR SEQ ID NO:55:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:55:

Xaa Val Xaa Pro Pro Val Lys
1               5

( 2 ) INFORMATION FOR SEQ ID NO:56:

( i ) SEQUENCE CHARACTERISTICS:
( A ) LENGTH: 7 amino acids
( B ) TYPE: amino acid (C) STRANDEDNESS:
(D) TOPOLOGY: linear (ii) MOLECULE TYPE: peptide (xi) SEQUENCE DESCRIPTION: SEQ ID NO:56:

Xaa Val Xaa Pro Pro Val Phe
1               5

(2) INFORMATION FOR SEQ ID NO:57:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:57:

Xaa Val Xaa Pro Pro Val Tyr
1               5

(2) INFORMATION FOR SEQ ID NO:58:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:58:

Xaa Val Xaa Pro Pro Ile
1               5

(2) INFORMATION FOR SEQ ID NO:59:

(i) SEQUENCE CHARACTERISTICS:
(A) LENGTH: 6 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:59:

Xaa Val Xaa Pro Pro Leu
1               5

ANTITUMOR PEPTIDES

This application is a continuation-in-part of application Ser. No. 08/431,795, filed May 1, 1995, now abandoned, which is a continuation of application Ser. No. 07/985,696 filed Nov. 25, 1992, now abandoned, which is a continuation-in-part of application Ser. No. 07/885,788 filed May 20, 1992, now abandoned.

BACKGROUND OF THE INVENTION

It is known that peptides isolated from marine origin like Dolastatin-10 (U.S. Pat. No. 4,816,444) and Dolastatin-15 (EP-A-398558) show potent cell growth inhibitory activity (cf.: Biochem. Pharmacology 40, no. 8, 1859–64, 1990); J. Natl. Cancer Inst. 85, 483–88, 1993 and references cited therein). Based upon interesting results in experimental tumor systems in vivo, further preclinical evaluation of these natural products is currently under way in order to initiate clinical studies in cancer patients. However, the natural products have disadvantages, such as poor solubility in aqueous solvents and costly building blocks needed for synthesis. The invention described herein provides novel peptides and derivatives thereof which offer improved therapeutic potential for the treatment of neoplastic diseases as compared to Dolastatin-10 and Dolastatin-15. Furthermore, the compounds of this invention may be conveniently synthesized as described in detail below.

DETAILED DESCRIPTION OF THE INVENTION

Figure 1:
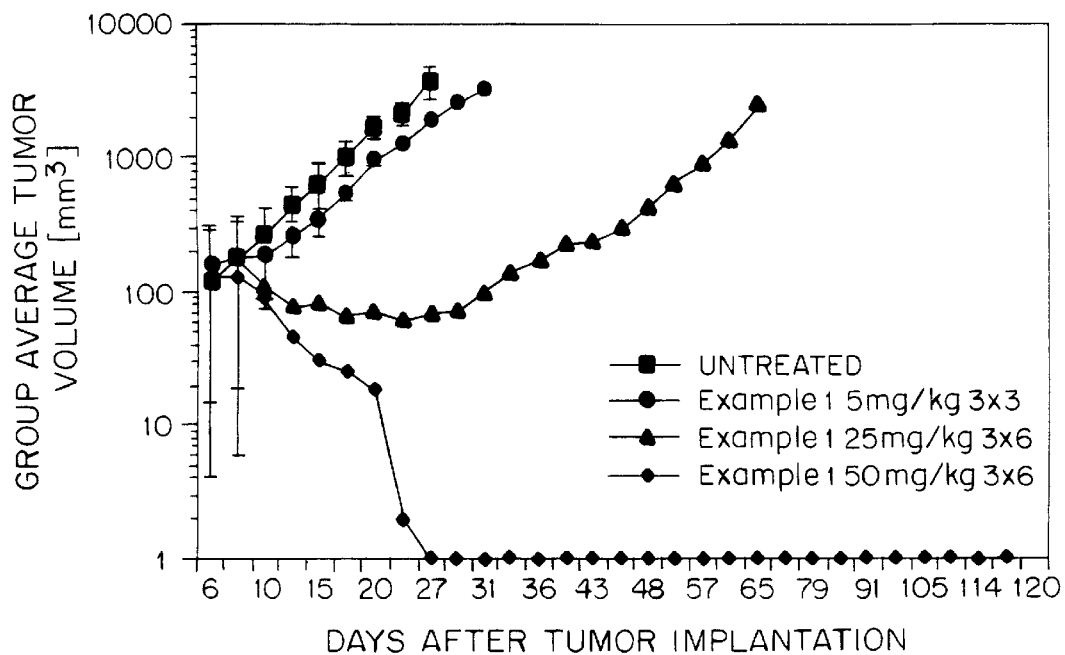

Compounds of this invention include novel peptides of the formula I

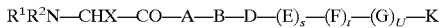

$$R^1R^2N\text{---}CHX\text{---}CO\text{---}A\text{---}B\text{---}D\text{---}(E)_s\text{---}(F)_t\text{---}(G)_u\text{---}K \quad \text{I}$$

where
- $R^1$ is alkoxy, preferably $C_1$–$C_4$; alkyl, preferably $C_{1-7}$; cycloalkyl, preferably $C_{3-6}$; alkylsulfonyl, preferably $C_{1-6}$; fluoroalkyl, preferably fluoroethyl, difluoroethyl, fluoroisopropyl, trifluoroisopropyl; aminosulfonyl which may be substituted by alkyl, preferably $C_{1-5}$; hydroxy; or benzyl which may be substituted by up to three substitutents independently selected from alkyl (preferably $C_{1-4}$), alkoxy (preferably $C_{1-4}$), nitro, halogen and $CF_3$;
- $R^2$ is hydrogen; alkyl, preferably $C_{1-4}$; fluoroalkyl, preferably fluoroethyl, difluoroethyl, fluoroisopropyl, trifluoroisopropyl; or cycloalkyl, preferably $C_{3-7}$;
- $R^1$—N—$R^2$ together may be a 5- or 6-membered heterocycle which may be unsubstituted or substituted with one or more substitutents independently selected from alkyl (preferably $C_{1-4}$), $N(CH_3)_2$, nitro, $CONH_2$ and COOEt;
- A is a valyl, isoleucyl, leucyl, allo-isoleucyl, 2,2-dimethylglycyl, 2-cyclopropylglycyl, 2-cyclopentylglycyl, 3-tert-butylalanyl, 2-tert-butylglycyl, 3-cyclohexylalanyl, 2-ethylglycyl, 2-cyclohexylglycyl, norleucyl or norvalyl residue;
- B is a N-alkyl-valyl, -norvalyl, -leucyl, -isoleucyl, -2-tert-butylglycyl, -3-tert-butylalanyl, -2-ethylglycyl, -2-cyclopentylglycyl, -2-cyclopentylglycyl, norleucyl or -2-cyclohexylglycyl residue where N-alkyl is preferably N-methyl or N-ethyl;
- D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;
- E is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;
- F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydroisoquinolyl-2-carbonyl, 3-thiazolylalanyl, 3-thienylalanyl, histidyl, 1-aminoindyl-1-carbonyl, 3-pyridylalanyl, 2-cyclohexylglycyl, norleucyl, norvalyl, neopentylglycyl, tryptophanyl, glycyl, alanyl, β-alanyl and 3-naphthylalanyl residues;
- x is hydrogen, alkyl (preferably $C_{1-5}$), cycloalkyl (preferablyl $C_{3-7}$), —$CH_2$-cyclohexyl or arylalkyl (preferably benzyl or phenethyl);
- s, t and u are independently 0 or 1; and
- K is hydroxy, alkoxy (preferably $C_{1-4}$), phenoxy, benzyloxy or a substituted or unsubstituted amino moiety;

and the salts thereof with physiologically tolerated acids.

This invention also provides methods for preparing the compounds of formula I, pharmaceutical compositions containing such compounds together with a pharmaceutically acceptable carrier and methods for using same for treating cancer in mammals.

One subclass of compounds of this invention includes compounds of formula I wherein $R^1$—N—$R^2$ is a pyrrolidinyl or piperidinyl residue which may be unsubstituted or substituted with one or more substituents which may independently be selected from alkyl (preferably $C_{1-4}$), $N(CH_3)_2$, nitro, oxo, $CONH_2$ and COOEt;

Another subclass of compounds of this invention includes compounds of formula I wherein K is an amino moiety of the formula $R^5$—N—$R^6$ wherein
- $R^5$ is hydrogen, or hydroxy, or $C_{1-7}$ alkoxy, or benzyloxy (which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, or $COONH_2$), or phenyloxy (which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, or $COONH_2$), or $C_{1-12}$-alkyl (which may be substituted by one or more fluoro atoms), or $C_{3-7}$-cycloalkyl, or benzyl (which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, or $COONH_2$);
- $R^6$ is hydrogen, or $C_{1-12}$ alkyl (which may be substituted by one or more fluoro atoms), or —$(CH_2)_v$, —$C_{3-7}$-cycloalkyl (v=0,1,2, or 3), or norephedryl, or norpseudoephedryl, or quinolyl, or pyrazyl, or —$CH_2$-benzimidazolyl, or adamantyl, or —$CH_2$-adamantyl, or alpha-methyl-benzyl, or alpha-dimethylbenzyl, or —$(CH_2)_v$-phenyl (v=0,1,2,or 3; which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl which may form a cyclic system, cyano, hydroxy, N(CH$_3$)$_2$, COOMe, COOEt, COOiPr, or COONH$_2$), or —(CH$_2$)$_m$-naphthyl (m=0 or 1; which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or —(CH$_2$)$_w$-benzhydryl (w=0,1, or 2; which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or biphenyl (which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or pyridyl (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or picolyl (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or —CH$_2$—CH$_2$-pyridyl (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or benzothiazolyl (which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or benzoisothiazolyl (which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or benzopyrazolyl (which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or benzoxazolyl (which may be substituted by up to three substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or —(CH$_2$)$_m$-fluorenyl (m=0 or 1; which may be substituted by up to three substituents which may independently be CF$_3$, nitro, C$_{1-7}$ alkylsulfonyl, C$_{1-4}$ alkoxy, halogen, C$_{1-4}$ -alkyl which may form a cyclic system, cyano, hydroxy, N(CH$_3$)$_2$, COOMe, COOEt, COOiPr, or COONH$_2$), or pyrimidyl (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, N(CH$_3$)$_2$, COOMe, COOEt, COOiPr, or COONH$_2$), or —(CH$_2$)$_m$-indanyl (m=0 or 1; which may be substituted by up to three substituents which may independently be CF$_3$, nitro, C$_{1-7}$ alkylsulfonyl, C$_{1-4}$ alkoxy, halogen, C1–4-alkyl which may form a cyclic system, cyano, hydroxy, N(CH$_3$)$_2$, COOMe, COOEt, COOiPr, or COONH$_2$), or —(CH$_2$CH$_2$O)$_y$—CH$_3$ (y=0,1,2,3,4, or 5), or —(CH$_2$CH$_2$O)$_y$—CH$_2$CH$_3$ (y=0,1,2,3,4, or 5), or —NH—C$_6$H$_5$ (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or —NCH$_3$—C$_6$H$_5$ (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or —NH—CH$_2$—C$_6$H$_5$ (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or —NCH$_3$—CH$_2$—C$_6$H$_5$ (which may be substituted by up to two substituents which may independently be CF$_3$, nitro, C$_{1-7}$ alkylsulfonyl, C$_{1-4}$ alkoxy, halogen, C$_{1-4}$-alkyl which may form a cyclic system, cyano, hydroxy, COOMe, COOEt, COOiPr, or COONH$_2$), or 5-membered heteroaryl which may be substituted by up to three substituents which may independently be CF$_3$, nitro, C$_{1-7}$ alkylsulfonyl, C$_{1-4}$ alkoxy, thiomethyl, thioethyl, picolyl, acetyl, C$_{3-6}$-cycloalkyl, thiophenyl, —CH$_2$—COOEt, C$_{3-4}$-alkylen group forming a bicyclic system with the heterocycle, phenyl (which may be substituted by up to three substituents which may independently be nitro, CF$_3$, CN, halogen, or C$_{1-4}$-alkyl), benzyl (which may be substituted by up to three substituents which may independently be nitro, CF$_3$, halogen, C$_{1-4}$-alkyl, C$_{1-7}$-alkylsulfonyl, cyano, hydroxy, C$_{1-4}$-dialkylamino), or —CHR$^7$-5-membered heteroaryl (which may be substituted by up to two subsituents which may independently be CF$_3$, nitro, cyano, halogen, COOMe, COOEt, COOiPr, CONH$_2$, C$_{1-4}$-alkyl, C$_{1-4}$-alkoxy, phenyl, benzyl, naphthyl, or C$_{1-7}$-alkylsulfonyl [R$^7$= hydrogen, linear or branched C$_{1-5}$ alkyl, benzyl; or R$^7$ and R$^5$ together form a group —(CH$_2$)$_3$—or —(CH$_2$)$_4$—]).

This subclass includes compounds of formula I wherein s, t and u are independently 0 or 1; R$^1$, R$^2$ and X are lower alkyl, A is a lower alkyl amino acid, B is a N-loweralkylated lower alkyl amino acid; D,E,F,G and K are as previously defined. With the foregoing in mind, three sets of such compounds can thus be depicted by the following formulas II, III, and IV:

R$^1$R$^2$N-CXH-CO-A-B-Pro-Pro-F-G-K      II

R$^1$R$^2$N-CXH-CO-A-B-Pro-Pro-F-K      III

R$^1$R$^2$N-CXH-CO-A-B-Pro-Pro-K      IV

—CHR$^7$-5-membered heteroaryl may for example be represented by one of the following residues:

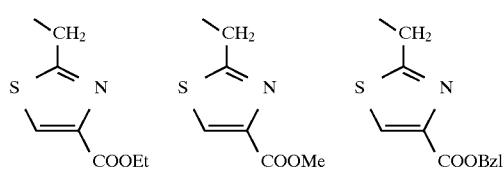
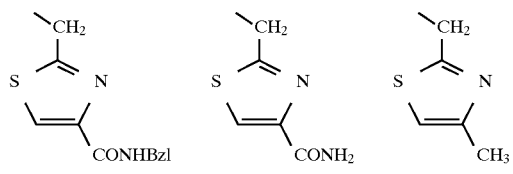
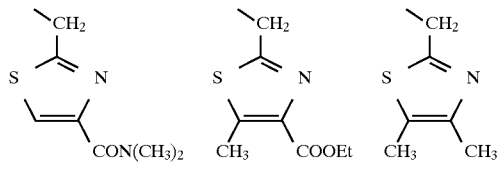
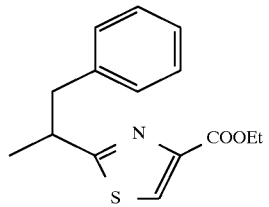
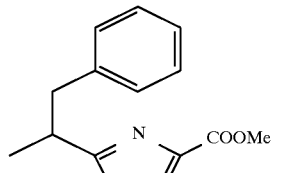
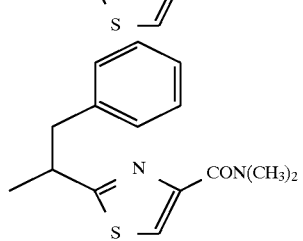
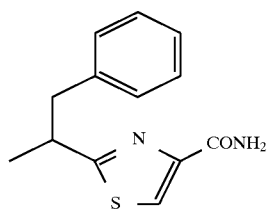
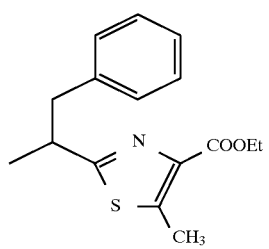
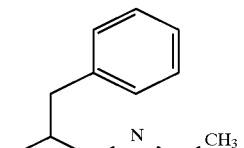
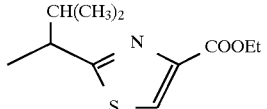
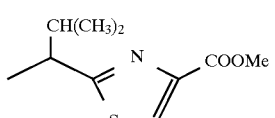
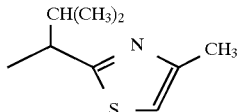
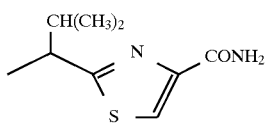
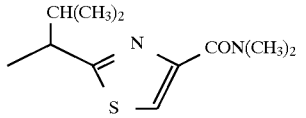
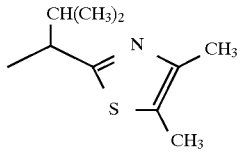
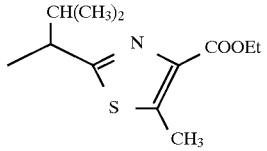
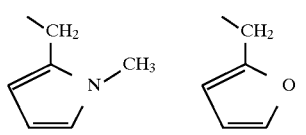

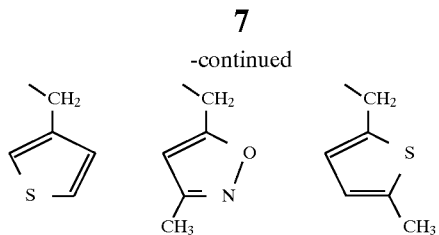
—NR⁵CHR⁷—5-membered heteroaryl may for example be represented by the following residues:
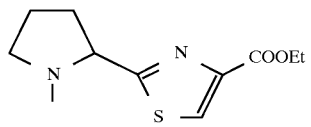
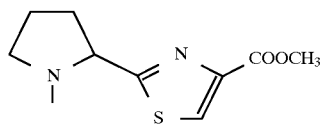
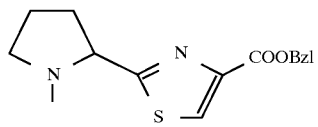
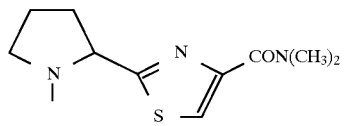
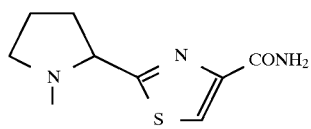
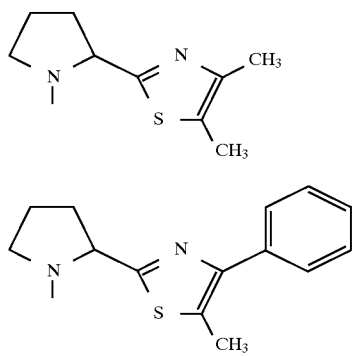
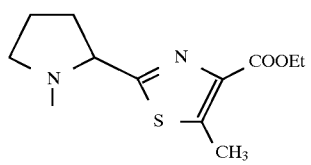
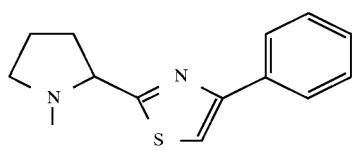
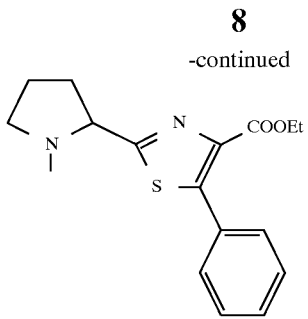
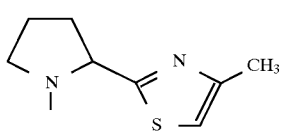
5-membered heteroaryl may for example be represented by the following residues:
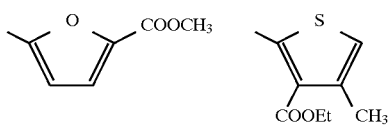
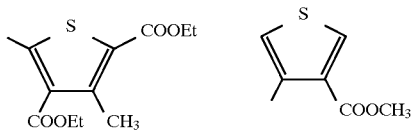
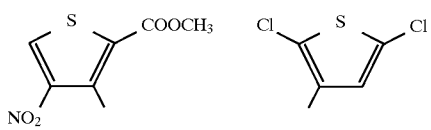
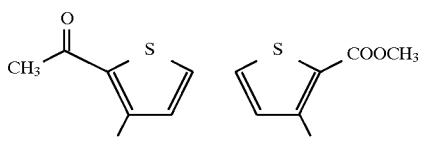
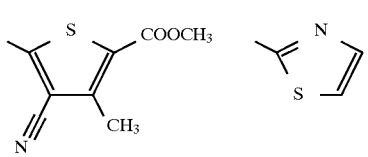
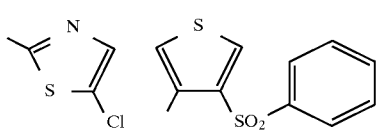
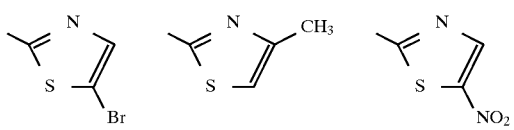
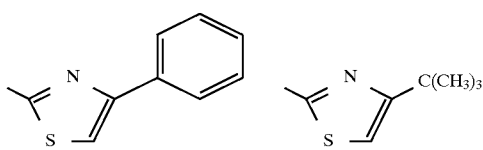

-continued
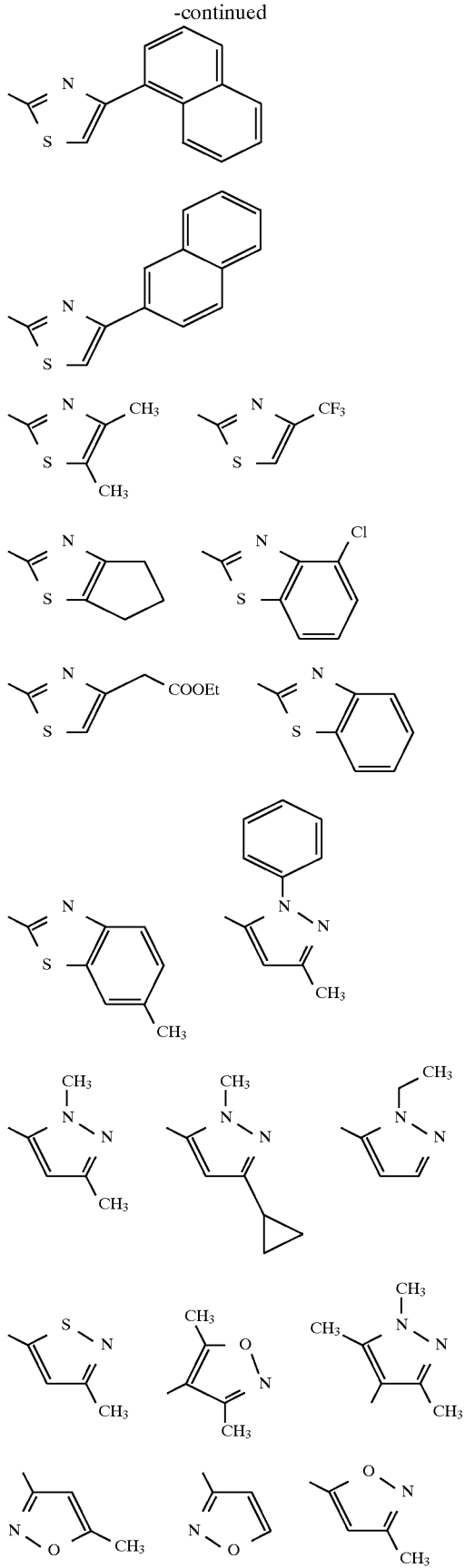
-continued
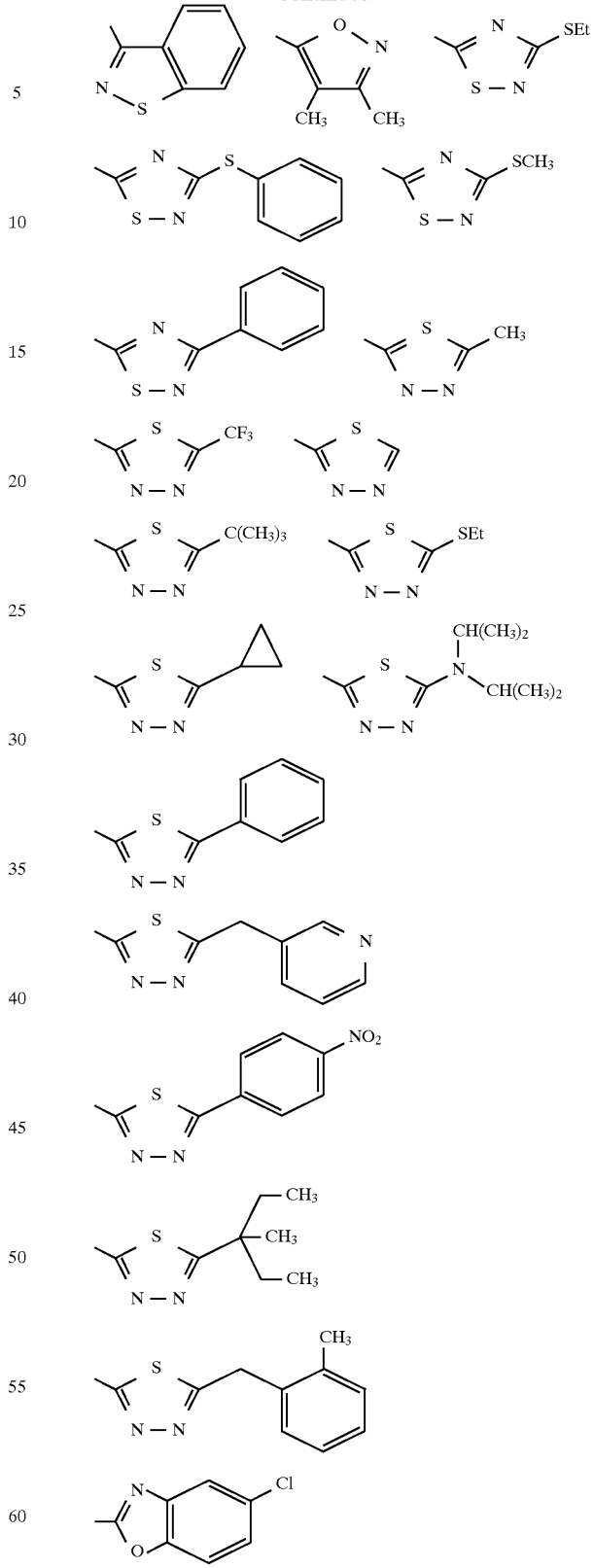
In another subclass of compounds of this invention R⁵—N—R⁶ together may form structures selected from the group consisting of

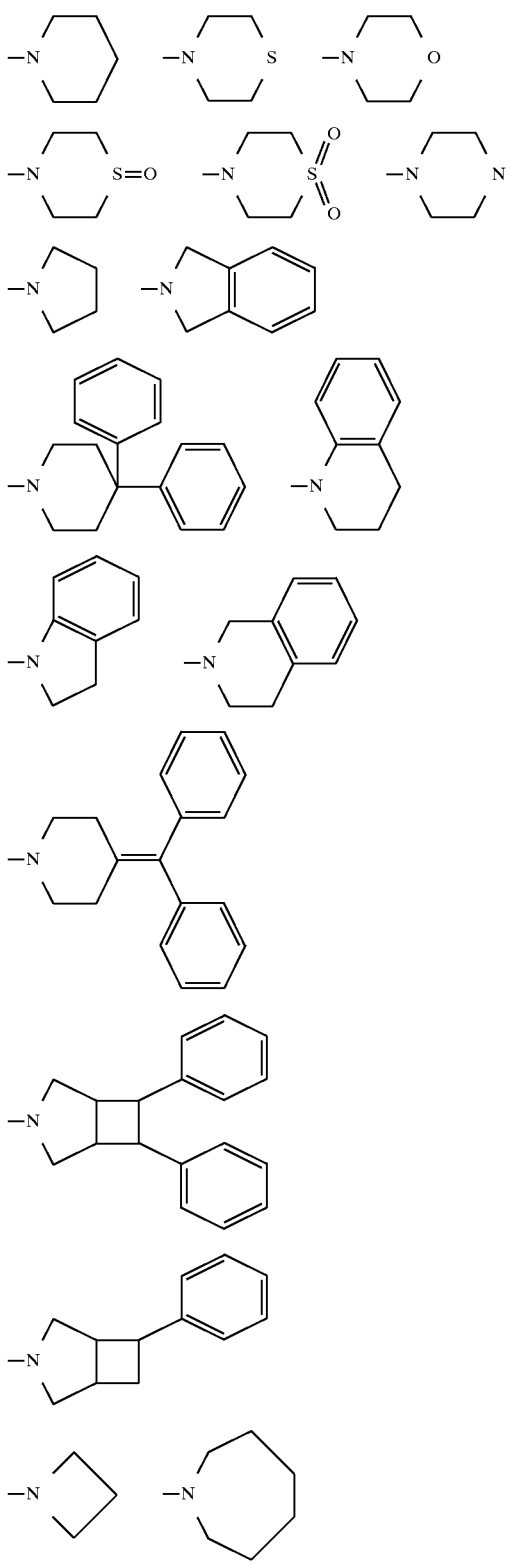

which may be unsubstituted or substituted with one or more substituents independently selected from the group consisting of $CF_3$, nitro, halogen, oxo, cyano, formyl, N,N-dimethylamino, $C_{1-6}$-alkyl, $C_{3-6}$-cycloalkyl, $C_{3-4}$-alkylen group forming a bicyclic system with the heterocycle, $C_{1-4}$-alkoxy, phenoxy, benzoxy, naphthyl, pyrimidyl, COOEt, pyrrolidinyl, piperidinyl, thienyl, pyrrolyl, $CH_2$—CO—$NCH(CH_3)_2$, —$CH_2$—CO—$N(CH_2)_4$, —$CH_2$—CO—N$(CH2)_4O$, benzyl (which may be substituted by up to three substituents independently selected from the group consisting of nitro, halogen, $CF_3$, thiomethyl or the corresponding sulfoxide or sulfone, thioethyl or the corresponding sulfoxide or sulfone, $C_{1-4}$-alkyl, and $C_{1-4}$-alkoxy).

Still another subclass of compounds of this invention includes for example compounds of formula I wherein s, t and u are 1 and K is a hydroxy, alkoxy, phenoxy or benzyloxy moiety.

Yet another subclass of compounds of this invention includes for example compounds of formula I wherein s and t are 1, u is 0 and K is a hydroxy, alkoxy, phenoxy or benzyloxy moiety.

Another subclass of compounds of this invention includes for example compounds of formula I wherein s is 1, t and u are 0 and K is a hydroxy, alkoxy, phenoxy or benzyloxy moiety.

These examples illustrate but do not limit the scope of the present invention.

The peptides of the formula I are composed preferably of L-amino acids but they may contain one or more D-amino acids.

The new compounds may be present as salts with physiologically tolerated acids such as: hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The novel compounds can be prepared by known methods of peptide chemistry. Thus, the peptides can be assembled sequentially from amino acids or by linking suitable small peptide fragments. In the sequential assemblage, starting at the C terminus the peptide chain is extended stepwise by one amino acid each time. In fragment coupling it is possible to link together fragments of different lengths, and the fragments in turn can be obtained by sequential assemblage from amino acids or themselves by fragment coupling.

Both in the sequential assemblage and in the fragment coupling it is necessary to link the units by forming an amide linkage. Enzymatic and chemical methods are suitable for this.

Chemical methods for forming the amide linkage are described in detail by Mueller, Methoden der organischen Chemie Vol. XV/2, pp 1 to 364, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976 and other standard works on peptide chemistry. Particular preference is given to the azide method, the symmetric and mixed anhydride method, in situ generated or preformed active esters, the use of urethane protected N-carboxy anhydrides of amino acids and the formation of the amide linkage using coupling reagents (activators, especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDCI), n-propanephosphonic anhydride (PPA), N,N-bis(2-oxo-3-oxazolldinyl)-amidophosphoryl chloride (BOP-Cl), bromo-tris-pyrrolidinophosphonium hexafluorophosphate (PyBrop), diphenylphosphoryl azide (DPPA), Castro's reagent (BOP, PyBop), 0-benzotriazolyl-N,N,N', N'-tetramethyluronium salts (HBTU), diethylphosphoryl cyanide (DEPCN), 2,5-diphenyl-2,3-dihydro-3-oxo-4-hydroxythiophene dioxide (Steglich's reagent; HOTDO)

and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), Azabenzotriazole, N-hydroxysuccinimide (HOSu) or 2-hydroxypyridine.

Whereas it is normally possible to dispense with protective groups in enzymatic peptide synthesis, reversible protection of reactive groups not involved in formation of the amide linkage is necessary for both reactants in chemical synthesis. Three conventional protective group techniques are preferred for the chemical peptide synthesis: the benzyloxycarbonyl (Z), the t-butoxycarbonyl (Boc) and the 9-fluorenylmethoxycarbonyl (Fmoc) techniques. Identified in each case is the protective group on the alpha-amino group of the chain-extending unit. A detailed review of amino-acid protective groups is given by Mueller, Methoden der organischen Chemie Vol. XV/1, pp 20 to 906, Thieme Verlag, Stuttgart, 1974. The units employed for assembling the peptide chain can be reacted in solution, in suspension or by a method similar to that described by Merrifield in J. Amer. Chem. Soc. 85 (1963) 2149. Particularly preferred methods are those in which peptides are assembled sequentially or by fragment coupling using the Z, Boc or Fmoc protective group technique, with one of the reactants in the said Merrifield technique being bonded to an insoluble polymeric support (also called resin hereinafter). This typically entails the peptide being assembled sequentially on the polymeric support using the Boc or Fmoc protective group technique, the growing peptide chain being covalently bonded at the C terminus to the insoluble resin particles (cf. FIG. 1 and 2). This procedure makes it possible to remove reagents and byproducts by filtration, and thus recrystallization of intermediates is unnecessary.

The protected amino acids can be linked to any suitable polymers, which merely have to be insoluble in the solvents used and to have a stable physical form which makes filtration easy. The polymer must contain a functional group to which the first protected amino acid can be firmly attached by a covalent bond. Suitable for this purpose are a wide variety of polymers, eg. cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl-resin (Pam-resin), p-benzyloxy-benzyl-alcohol-resin, benzhydryl-amine-resin (BHA-resin), 4-(hydroxymethyl)-benzoyloxy-methyl-resin, the resin of Breipohl et al. (Tetrahedron Letters 28 (1987) 565; supplied by BACHEM), 4-(2,4-di-methoxyphenylaminomethyl) phenoxy-resin (supplied by Novabiochem) or o-chlorotrityl-resin (supplied by Biohellas).

Suitable for peptide synthesis in solution are all solvents which are inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of the said solvents. Peptide synthesis on the polymeric support can be carried out in all inert organic solvents in which the amino-acid derivatives used are soluble. However, preferred solvents additionally have resin-swelling properties, such as DMF, DCM, NMP, acetonitrile and DMSO, and mixtures of these solvents. After synthesis is complete, the peptide is cleaved off the polymeric support. The conditions under which cleavage off the various resin types is possible are disclosed in the literature. The cleavage reactions most commonly used are acid- and palladium-catalyzed, especially cleavage in liquid anhydrous hydrogen fluoride, in anhydrous trifluormoethane-sulfonic acid, in dilute or concentrated trifluoroacetic acid, palladium-catalyzed cleavage in THF or THF-DCM mixtures in the presence of a weak base such as morpholine or cleavage in acetic acid/dichloromethane/trifluoroethanol mixtures. Depending on the chosen protective groups, these may be retained or likewise cleaved off under the cleavage conditions. Partial deprotection of the peptide may also be worthwhile when certain derivatization reactions are to be carried out. Peptides dialkylated at the N-terminus can be prepared either by coupling on the appropriate N,N-dialkylamino acids in solution or on the polymeric support or by reductive alkylation of the resin-bound peptide in DMF/1% acetic acid with $NaCNBH_3$ and the appropriate aldehydes. The various non-naturally occurring amino acids as well as the various non-amino acid moieties disclosed herein may be obtained from commercial sources or synthesized from commercially-available materials using methods known in the art. For example, amino acids building blocks with $R_1$ and $R_2$ moieties can be prepared according to E. Wuensch, Houben Weyl, Meth. d. Org. Chemie, Bd. XV, 1, p. 306 following, Thieme Verlag Stuttgart 1974 and Literature cited therein. Peptides with gamma- or delta-lactam bridges can be prepared by incorporating the appropriate lactam-bridged dipeptide units (R. Freidinger, J. Org. Chem. (1982) 104–109) into the peptide chain. Peptides with thiazole-, oxazol-, thiazolin- or oxazolin-containing dipeptide building blocks can be prepared by incorporating the appropriate dipeptidic units (P. Jouin et al., Tetrahedron Letters (1992), 2807–2810; P. Wipf et al., Tetrahedron Letters (1992), 907–910; W.R. Tully, J. Med. Chem. (1991), 2065; Synthesis (1987), 235) into the peptide chain.

The compounds of this invention may be used to inhibit or otherwise treat solid tumors (e.g. tumors of the lung, breast, colon, prostate, bladder, rectum, or endometrial tumors) or hematological malignancies (e.g. leukemias, lymphomas) by administration of the compound to the mammal. Administration may be by any of the means which are conventional for pharmaceutical, preferably oncological, agents, including oral and parenteral means such as subcutaneously, intravenously, intramuscularly and intraperitoneally. The compounds may be administered alone or in the form of pharmaceutical compositions containing a compound of formula I together with a pharmaceutically accepted carrier appropriate for the desired route of administration. Such pharmaceutical compositions may be combination products, i.e., may also contain other therapeutically active ingredients.

The dosage to be administered to the mammal will contain an effective tumor-inhibiting amount of active ingredient which will depend upon conventional factors including the biological activity of the particular compound employed; the means of administration; the age, health and body weight of the recipient; the nature and extent of the symptoms; the frequency of treatment; the administration of other therapies; and the effect desired. A typical daily dose will be about 0.05 to 100 milligrams per kilogram of body weight, preferably 0.1 to 10 milligrams, on oral administration and about 0.01 to 100 milligrams per kilogram of body weight, preferably 0.05 to 50 milligrams, on parenteral administration.

The novel compounds can be administered in conventional solid or liquid pharmaceutical administration forms, e.g. uncoated or (film-)coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sucker et al.: Pharmazeutische Technologie, Thieme-Verlag, Stuttgart, 1978). The administration forms obtained in this way normally contain 1–90% by weight of the active substance.

The following examples are intended to illustrate the invention. The proteinogenous amino acids are abbreviated in the examples using the known three-letter code. Other meanings are: TFA=trifluoroacetic acid, Ac=acetic acid, Bu=butyl, Et=ethyl, Me=methyl, Bzl=benzyl, Nal=3-naphthylalanine, Cha=3-cyclohexylalanine, Npg=neopentylglycine, Abu=2-amino butyryl, Dab=2,4-diaminobutyryl. iPr=isopropyl.

A. General procedures

I. The peptides claimed in claim 1 are either synthesized by classical solution synthesis using standard Z- and Boc-methodology as described above or by standard methods of solid-phase synthesis on a completely automatic model 431A synthesizer supplied by APPLIED BIOSYSTEMS. The apparatus uses different synthetic cycles for the Boc and Fmoc protective group techniques.

| a) Synthetic cycle for the Boc protective group technique | |
|---|---|
| 1. 30% trifluoroacetic acid in DCM | 1 × 3 min |
| 2. 50% trifluoroacetic acid in DCM | 1 × 1 min |
| 3. DCM washing | 5 × 1 min |
| 4. 5% diisopropylethylamine in DCM | 1 × 1 min |
| 5. 5% diisopropylethylamine in NMP | 1 × 1 min |
| 6. NMP washing | 5 × 1 min |
| 7. Addition of preactivated protected amino acid (DCC and 1 equivalent of HOBt in NMP/DCM); Peptide coupling (1st part) | 1 × 30 min |
| 8. Addition of DMSO to the reaction mixture until it contains 20% DMSO by volume Peptide coupling (2nd part) | 1 × 16 min |
| 9. Addition of 3.8 equivalents of diisopropylethylamine to the reaction mixture Peptide coupling (3rd part) | 1 × 7 min |
| 10. DCM washing | 3 × 1 min |
| 11. if conversion is incomplete, repetition of coupling (back to 6.) | |
| 12. 10% acetic anhydride, 5% diisopropylethylamine in DCM | 1 × 2 min |
| 13. 10% acetic anhydride in DCM | 1 × 4 min |
| 14. DCM washing | 4 × 1 min |
| 15. back to 1. | |

BOP-Cl and PyBrop were used as reagents for coupling of the amino acid following N-methylamino acids. The reaction times were correspondingly increased. In solution synthesis, the use of either Boc-protected amino acid NCAs (N-tert.-butyloxycarbonyl-amino acid-N-carboxy-anhydrides) or Z-protected amino acid NCAs (N-benzyloxycarbonyl-amino acid-N-carboxy-anhydrides) respectively is most advantageous for this type of coupling.

| b) Synthetic cycle for the Fmoc protective group technique | |
|---|---|
| 1. DMF washing | 1 × 1 min |
| 2. 20% piperidine in DMF | 1 × 4 min |
| 3. 20% piperidine in DMF | 1 × 16 min |
| 4. DMF washing | 5 × 1 min |
| 5. Addition of the preactivated protected amino acid (activation by 1 equivalent of TBTU and 5 equivalents of DIPEA in DMF); Peptide coupling | 1 × 61 min |
| 6. DMF washing | 3 × 1 min |
| 7. if conversion is incomplete, repetition of coupling (back to 5.) | |
| 8. 10% acetic anhydride in DMF | 1 × 8 min |
| 9. DMF washing | 3 × 1 min |
| 10. back to 2. | |

BOP-Cl and PyBrop were used as reagents for coupling on the amino acid following the N-methylamino acids. The reaction times were correspondingly increased.

II. Reductive alkylation of the N terminus

The peptide-resin prepared as in AIa or AIb was deprotected at the N terminus (steps 2–4 in AIb or 1–6 in AIa) and then reacted with a 3-fold molar excess of aldehyde or ketone in DMF/1% acetic acid with addition of 3 equivalents of $NaCNBH_3$. After reaction was complete (negative Kaiser test) the resin was washed several times with water, isopropanol, DMF and dichloromethane.

III. Workup of the peptide-resins obtained as in Ia and II

The peptide-resin was dried under reduced pressure and transferred into a reaction vessel of a TEFLON HF apparatus (supplied by PENINSULA). Addition of a scavenger, preferably anisole (1 ml/g of resin), and in the case of tryptophan-containing peptides of a thiol to remove the indolic formyl group, preferably ethanedithiol (0.5 ml/g of resin), was followed by condensing in hydrogen fluoride (10 ml/g of resin) while cooling with liquid $N_2$. The mixture was left to warm to 0° C. and stirred at this temperature for 45 min. The hydrogen fluoride was then stripped off under reduced pressure, and the residue was washed with ethyl acetate in order to remove remaining scavenger. The peptide was extracted with 30% acetic acid and filtered, and the filtrate was lyophilized.

IV. Work-up of the peptide-resins obtained as in Ib and II

The peptide-resin was dried under reduced pressure and then subjected to one of the following cleavage procedures, depending on the amino-acid composition (Wade, Tregear, Howard Florey Fmoc Workshop Manual, Melbourne 1985).

Cleavage conditions:

| TFA | Scavenger | Reaction time |
|---|---|---|
| 1. 95% | 5% water | 1.5 h |
| 2. 95% | 5% ethanethiol/anisol (1:3) | 1.5 h |

The suspension of the peptide-resin in the suitable TFA mixture was stirred at room temperature for the stated time and then the resin was filtered off and washed with TFA and DCM. The filtrate and the washings were concentrated, and the peptide was precipitated by addition of diethyl ether. After cooling in an ice bath, the precipitate was filtered off, taken up in 30% acetic acid and lyophilized.

V. When an o-chlorotrityl-resin (supplied by Biohellas) is used, the suspension of the peptide-resin in an acetic acid/trifluoroethanol/dichloromethane mixture (1:1:3) is stirred at room temperature for 1 h. The resin is then filtered off with suction and thoroughly washed with the cleavage solution. The combined filtrates are concentrated in acuo and treated with water. The precipitated solid is removed by filtration or centrifugation, washed with diethyl ether and dried under reduced pressure.

VI. Purification and characterization of the peptides

Purification was carried out by gel chromatography (SEPHADEX G-10, G-15/10% HOAc, SEPHADEX LH20/MeOH) with or without subsequent medium pressure chromatography (stationary phase: HD-SIL C-18, 20–45 mikron, 100 Angstrom; mobile phase: gradient with A=0.1% TFA/MeOH, B=0.1% TFA/water).

The purity of the resulting products was determined by analytical HPLC (stationary phase: 100 2.1 mm VYDAC C-18, 5 1, 300 A; mobile phase: acetonitrile-water gradient, buffered with 0.1% TFA, 40° C.).

Characterization was by amino-acid analysis and fast atom bombardment mass spectroscopy.

B. Specific procedures

EXAMPLE 1
(SEQ ID NO: 1)

N,N-Dimethyl-Val-Val-N-methyl-Val-Pro-Pro-Val-Phe-NH$_2$ 1.98 g of Fmoc-RINK-resin (substitution 0.46 mmol/g), corresponding to a batch size of 0.84 mmol, were reacted as in AIb with 1.26 mmol each of Fmoc-Phe-OH
Fmoc-Val-OH
Fmoc-Pro-OH
Fmoc-Pro-OH
Fmoc-N-methyl-Val-OH
Fmoc-Val-OH
Fmoc-Val-OH The amino acid following the N-methylamino acid was coupled on with PyBrop as coupling reagent. After the iterative synthetic cycles were completed, the peptide-resin underwent N-terminal deprotection (steps 2–4 in AIb), and was further reacted with aqueous formaldehyde solution as in AII and then dried under reduced pressure. The resulting resin was subjected to TFA cleavage as in AIV. The crude product (590 mg) was purified by gel filtration (SEPHADEX-LH-20). The yield was 295 mg.

EXAMPLE 1 can also be prepared via classical solution phase methodology. The synthesis of N,N-Dimethyl-Val-Val-N-Methyl-Val-Pro-Pro-Val-Phe-NH$_2$ and its various intermediates is described in the following paragraph.

a) Z-MeVal-Pro-OMe 66.25 g (250 mmol) Z-MeVal-OH were dissolved in 250 ml dry dichloromethane. After addition of 36.41 ml (262.5 mmol) triethylamine, the reaction mixture was cooled to −25° C. and 32.27 ml (262.5 mmol) pivaloyl chloride were added.

After stirring for 2,5 h, 41.89 g (250 mmol) H-Pro-OMe×HCl in 250 ml dichloromethane, neutralized with 36.41 ml (262.5 mmol) triethylamine at 0° C., were added to the reaction mixture. Stirring continued for 2 h at −25° C. and overnight at room temperature. The reaction mixture was diluted with dichloromethane and thoroughly washed with saturated aqueous NaHCO$_3$ solution (3×), water (1×), 5% citric acid (3×) and saturated NaCl solution. The organic phase was dried over sodium sulfate and evaporated to dryness. The residue (91.24 g) was stirred with petroleum ether overnight and filtered. 62.3 g of product were obtained.

b) H-MeVal-Pro-OMe 48.9 g (130 mmol) Z-MeVal-Pro-OMe were dissolved in 490 ml methanol. After addition of 10.9 ml (130 mmol) concentrated hydrochloric acid and 2.43 g 10 % Palladium/charcoal, the reaction mixture was hydrogenated. Filtration and evaporation to dryness yielded 36.43 g of the product.

c) Z-Val-MeVal-Pro-OMe 18.1 g (65 mmol) H-MeVal-Pro-OMe, 21.6 g (78 mmol) Z-Val-N-carboxyanhydride and 22.8 ml (130 mmol) diisopropylethylamine were stirred in 110 ml DMF at 40° C. for 2 d. After evaporation of DMF, dichloromethane was added and the organic phase washed with saturated aqueous NaHCO$_3$ solution (3×), water (1×), 5% citric acid (3×) and saturated NaCl solution. The organic phase was dried over sodium sulfate and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml methanol. After addition of 1.15 g 10% Palladium/charcoal, the reaction mixture was hydrogenated. Filtration and evaporation to dryness yielded 21.96 g of the product.

e) Z-Val-Val-MeVal-Pro-OMe 15.29 g (61 mmol) Z-Val-OH and 21.96 g (61 mmol) H-Val-MeVal-Pro-OMe were dissolved in 610 ml dichloromethane and cooled to 0° C. After addition of 8.16 ml (73.2 mmol) N-Methylmorpholine, 2.77 g (20.3 mmol) HOBt and 11.74 g (61 mmol) EDCI, the reaction mixture was stirred overnight at room temperature, diluted with dichloromethane and thoroughly washed with saturated aqueous NaHCO$_3$ solution (3×), water (1×), 5% citric acid (3×) and saturated NaCl solution. The organic phase was dried over sodium sulfate and evaporated to dryness to yield 31.96 g of the product.

f) Z-Val-Val-MeVal-Pro-OH 31.96 g (57 mmol) Z-Val-Val-MeVal-Pro-OMe were dissolved in 250 ml methanol. 102.6 ml of a 1 N LiOH solution was added and the mixture stirred overnight at room temperature. After addition of 500 ml water, the aqueous phase was washed three times with ethyl acetate, adjusted to pH 2 at 0° C. and extracted three times with ethyl acetate. The organic phase was dried over sodium sulfate and evaporated to dryness yielding 30.62 g of the desired product as a white solid.

g) Z-Val-Val-MeVal-Pro-Pro-Val-Phe-NH$_2$ 25 g (43.3 mmol) Z-Val-Val-MeVal-Pro-OH and 15.59 g (43.3 mmol) H-Pro-Val-Phe-NH$_2$ were suspended in 430 ml of dry dichloromethane. After cooling to 0° C., 5.81 ml (52 mmol) N-methylmorpholine, 1.97 g (15 mmol) HOBt and 8.33 g (43.3 mmol) EDCI were added and the reaction mixture stirred overnight at room temperature. The solvents were evaporated, the residue dissolved in 640 ml dichloromethane and thoroughly washed with saturated aqueous NaHCO$_3$ solution (4×), water (1×), 5% citric acid (3×) and saturated NaCl solution. The organic phase was dried over sodium sulfate and evaporated to dryness to yield 33.04 g of the product. The crude product was chromatographed on a silica gel column with 20% MeOH/Hexane. 18.32 g of the desired product were obtained.

h) N,N-Dimethyl-Val-Val-MeVal-Pro-Pro-Val-Phe-NH$_2$ 18.32 g Z-Val-Val-MeVal-Pro-Pro-Val-Phe-NH$_2$ were dissolved in 80 ml methanol. 0.4 g 10% Pd/C were added under nitrogen atmosphere and the reaction mixture hydrogenated at room temperature for 4 h. After addition of 6.22 ml (81.24 mmol) of a 37% aqueous formaldehyde solution, hydrogenation was continued for 5 h. Filtration and evaporation of the solvent gave rise to 15.6 g of crude product. Further purification was achieved by dissolving the peptide in water, adjusting the pH to 2 and extracting the aqueous phase three times with ethyl acetate. The aqueous phase was then adjusted to pH 8–9 and extracted four times with ethyl acetate. The organic phase was washed with water and dried over sodium sulfate to yield 11.3 g of purified product as a white powder. The compound was characterized by fast atom bombardment mass spectrometry ([M+H]$^+$=797).

EXAMPLE 2
(SEQ ID NO: 2)

N,N-Dimethyl-Val-Val-N-Me-Val-Pro-{1-[thiazol-(2)-yl]-2-phenyl}-ethylamide 4.11 g of Fmoc-Pro-p-alkoxybenzyl-alcohol-resin (substitution 0.73 mmol/g), corresponding to a batch size of 3 mmol, were reacted as in AIb with 4.5 mmol each of Fmoc-N-MeVal-OH Fmoc-Val-OH Fmoc-Val-OH.

The amino acid following the N-methylamino acid was in this case reacted with double coupling using PyBrop or Bop-Cl with increased reaction times. After the synthesis was complete, the peptide-resin underwent N-terminal deprotection (steps 2–4 in AIb), and was further reacted with aqueous formaldehyde solution as in AII and then dried under reduced pressure. The resin obtained in this way was subjected to TFA cleavage as in AIV. The crude product (750 mg) was employed directly for the next coupling. 100 mg of this compound were reacted with 45 mg of (S)-2-[1-amino-2-phenylethyl] thiazole and 230 mg of PyBop with the addition of 192 mikroL of DIPEA in DMF at room temperature for 2 d. The reaction mixture was purified by gel chromatography (Sephadex LH-20, methanol) and the product fractions were combined. 83 mg of product were obtained.

The following compounds were prepared and can be prepared according to examples 1 and 2:

3. Xaa Val Xan Pro Pro Val Phe
4. Xaa Val Xan Pro Pro Val Xac
5. Xaa Val Xan Pro Pro Val Xad
6. Xaa Val Xan Pro Pro Val Xae
7. Xaa Val Xan Pro Pro Val Xaf
8. Xaa Val Xan Pro Pro Val His NH$_2$
9. Xbo Val Xan Pro Pro Val Phe NH$_2$
10. Xaa Val Xan Pro Pro Val Xag NH$_2$
11. Xaa Val Xan Pro Pro Val Xah
12. Xaa Xbe Xan Pro Pro Val Trp NH$_2$
13. Xaa Val Xan Pro Pro Xai Phe NH$_2$
14. Xae Val Xan Pro Pro Ile Phe NH$_2$
15. Xaa Val Xan Pro Xal Val Phe NH$_2$
16. Xaa Val Xan Pro Xak Val Phe NH$_2$
17. Xaa Val Xan Xak Pro Val Phe NH$_2$
18. Xaa Val Xan Xal Pro Val Phe NH$_2$
19. Xaa Val Xao Pro Pro Val Phe NH$_2$
20. Xaa Val Xam Pro Pro Val Phe NH$_2$
21. Xaa Xap Pro Pro Val Phe NH$_2$
22. Xaa Xaq Pro Pro Val Phe NH$_2$
23. Xaa Ile Xan Pro Pro Val Phe NH$_2$
24. Xaa Xai Xan Pro Pro Val Phe NH$_2$
25. Xaa Leu Xan Pro Pro Val Phe NH$_2$
26. Xar Val Xan Pro Pro Val Phe NH$_2$
27. Xas Val Xan Pro Pro Val Phe NH$_2$
28. Xat Val Xan Pro Pro Val Phe NH$_2$
29. Xau Val Xan Pro Xal Val Phe NH$_2$
30. Xav Val Xan Pro Pro Val Phe NH$_2$
31. Xan Val Xan Pro Pro Val Phe NH$_2$
32. Xaw Val Xan Pro Pro Val Phe NH$_2$
33. Xax Vai Xan Pro Pro Val Phe NH$_2$
34. Xaa Val Xan Pro Pro Phe Phe NH$_2$
35. Xaz Val Xan Pro Pro Val Phe NH$_2$
36. Xba Val Xan Pro Pro Val Phe NH$_2$
37. Xaa Val Xan Pro Pro Val NH$_2$
38. Xaa Val Xan Pro Xbb
39. Xaa Val Xan Pro Xbc
40. Xaa Val Xan Pro Pro Xbd
41. Xax Val Xan Pro Pro Val NH$_2$
42. Xaw Val Xan Pro Pro Val NH$_2$
43. Xat Val Xan Pro Pro Val NH$_2$
44. Xaa Xai Xan Pro Pro Val NH$_2$
45. Xaa Val Xan Pro Pro Xal NH$_2$
46. Xaa Val Xan Xak Pro Val NH$_2$
47. Xaa Val Xan Pro Xak Val NH$_2$
48. Xaa Val Xan Pro Pro Val
49. Xav Val Xan Pro Pro Val NH$_2$
50. Xaa Val Xan Pro Pro NH$_2$
51. Xaa Val Xan Pro Pro
52. Xaa Val Xan Pro Xbf
53. Xaa Val Xan Xbb
54. Xaa Val Xan Xbc
55. Xaa Val Xan Xbg
56. Xaa Val Xan Xbh
57. Xaa Val Xan Xbi
58. Xaa Val Xan Xbk
59. Xaa Val Xan Xbl
60. Xaa Val Xan Xbm
61. Xaa Val Xan Xbn
62. Xax Val Xan Pro Pro NH$_2$
63. Xaw Val Xan Pro Pro NH$_2$
64. Xbo Val Xan Pro Pro NH$_2$
65. Xat Val Xan Pro Pro NH$_2$
66. Xaa Xai Xan Pro Pro NH$_2$
67. Xat Xai Xan Pro Pro NH$_2$
68. Xaa Xap Pro Pro NH$_2$
69. Xaa Xaq Pro Pro NH$_2$
70. Xav Val Xan Pro Pro NH$_2$
71. Xaa Xap Pro NH$_2$
72. Xaa Xaq Pro NH$_2$
73. Xaa Val Xan Pro
74. Xaa Val Xbp
75. Xaa Val Xbq
76. Xaa Val Xbr
77. Xaa Val Xbs
78. Xaa Val Xan Xbf
79. Xaa Val Xbt
80. Xaa Val Xbu
81. Xaa Val Xbv
82. Xaa Val Xbw
83. Xax Val Xan Pro NH$_2$
84. Xbo Val Xan Pro NH$_2$
85. Xav Val Xan Pro NH$_2$
86. Xaa Val Xan Pro Xbn
87. Xaa Val Xan Pro Xbg
88. Xaa Val Xan Pro Xbi
89. Xaa Val Xan Pro Xbl
90. Xbo Val Xan Pro Xbg
91. Xbo Val Xan Pro Xbl
92. Xbo Xbe Xan Pro Xbg
93. Xaa Val Xan Pro Xbx
94. Xaa Xbe Xan Pro Pro NH$_2$
95. Xby Val Xan Pro Pro Val Phe NH$_2$
96. Xed Val Xan Pro Pro Val Phe NH$_2$
97. Xee Val Xan Pro Pro Val Phe NH$_2$
98. Xef Val Xan Pro Pro Val Phe NH$_2$
99. Xbz Val Xan Pro Pro Val Phe NH$_2$
100. Xeg Val Xan Pro Pro Val Phe NH$_2$
101. Xca Val Xan Pro Pro Val Phe NH$_2$
102. Xcb Val Xan Pro Pro Val Phe NH$_2$
103. Xcb Val Xao Pro Pro Val Phe NH$_2$

| | |
|---|---|
| 104. Xcc Val Xan Pro Pro Val Phe NH$_2$ | 172. Xaa Val Xan Pro Pro Val Xft |
| 105. Xce Val Xan Pro Pro Val Phe NH$_2$ | 173. Xaa Val Xan Pro Pro Val Xfw |
| 107. Xcg Val Xan Pro Pro Val Phe NH$_2$ | 174. Xaa Val Xan Pro Pro Val Xfx |
| 108. Xch Val Xan Pro Pro Val Phe NH$_2$ | 175. Xaa Val Xan Pro Pro Val Xga |
| 109. Xci Val Xan Pro Pro Val Phe NH$_2$ | 176. Xaa Val Xan Pro Pro Val Xgd |
| 110. Xck Val Xan Pro Pro Val Phe NH$_2$ | 177. Xaa Val Xan Pro Pro Val Xgg |
| 111. Xcl Val Xan Pro Pro Val Phe NH$_2$ | 178. Xaa Val Xan Pro Pro Val Xgh |
| 112. Xcm Val Xan Pro Pro Val Phe NH$_2$ | 179. Xaa Val Xan Pro Pro Val Xgl |
| 113. Xcn Val Xan Pro Pro Val Phe NH$_2$ | 180. Xaa Val Xan Pro Pro Val Xgl |
| 114. Xhn Val Xan Pro Pro Val Phe NH$_2$ | 181. Xaa Val Xan Pro Pro Val Xgs |
| 115. Xho Val Xan Pro Pro Val Phe NH$_2$ | 182. Xaa Val Xan Pro Pro Val Xgv |
| 116. Xhp Val Xan Pro Pro Val Phe NH$_2$ | 183. Xaa Val Xan Pro Pro Val Xhe |
| 117. Xhq Val Xan Pro Pro Val Phe NH$_2$ | 184. Xaa Val Xan Pro Pro Val Xgy |
| 118. Xby Val Xan Pro Pro Val NH$_2$ | 185. Xaa Val Xan Pro Pro Val Xhd |
| 119. Xed Val Xan Pro Pro Val NH$_2$ | 186. Xaa Val Xan Pro Pro Val Xhb |
| 120. Xee Val Xan Pro Pro Val NH$_2$ | 187. Xaa Val Xan Pro Pro Val Xhc |
| 121. Xef Val Xan Pro Pro Val NH$_2$ | 188. Xaa Val Xan Pro Pro Val Xhl |
| 122. Xbz Val Xan Pro Pro Val NH$_2$ | 189. Xaa Val Xan Pro Pro Xeh |
| 123. Xeg Val Xan Pro Pro Val NH$_2$ | 190. Xaa Val Xan Pro Pro Xen |
| 124. Xca Val Xan Pro Pro Val NH$_2$ | 191. Xaa Val Xan Pro Pro Xeo |
| 125. Xcb Val Xan Pro Pro Val NH$_2$ | 192. Xaa Val Xan Pro Pro Xep |
| 126. Xcc Val Xan Pro Pro Val NH$_2$ | 193. Xaa Val Xan Pro Pro Xeq |
| 127. Xce Val Xan Pro Pro Val NH$_2$ | 194. Xaa Val Xan Pro Pro Xer |
| 128. Xcs Val Xan Pro Pro Val NH$_2$ | 195. Xaa Val Xan Pro Pro Xet |
| 129. Xch Val Xan Pro Pro Val NH$_2$ | 196. Xaa Val Xan Pro Pro Xeu |
| 130. Xci Val Xan Pro Pro Val NH$_2$ | 197. Xaa Val Xan Pro Pro Xes |
| 131. Xck Val Xan Pro Pro Val NH$_2$ | 198. Xaa Val Xan Pro Pro Xew |
| 132. Xcl Val Xan Pro Pro Val NH$_2$ | 199. Xaa Val Xan Pro Pro Xez |
| 133. Xcm Val Xan Pro Pro Val NH$_2$ | 200. Xaa Val Xan Pro Pro Xfc |
| 134. Xcn Val Xan Pro Pro Val NH$_2$ | 201. Xaa Val Xan Pro Pro Xff |
| 135. Xhn Val Xan Pro Pro Val NH$_2$ | 202. Xaa Val Xan Pro Pro Xfl |
| 136. Xho Val Xan Pro Pro Val NH$_2$ | 203. Xaa Val Xan Pro Pro Xfs |
| 137. Xhp Val Xan Pro Pro Val NH$_2$ | 204. Xaa Val Xan Pro Pro Xfz |
| 138. Xhq Val Xan Pro Pro Val NH$_2$ | 205. Xaa Val Xan Pro Pro Xgc |
| 139. Xby Val Xan Pro Pro NH$_2$ | 206. Xaa Val Xan Pro Pro Xgf |
| 140. Xed Val Xan Pro Pro NH$_2$ | 207. Xaa Val Xan Pro Pro Xgm |
| 141. Xee Val Xan Pro Pro NH$_2$ | 208. Xaa Val Xan Pro Pro Xgr |
| 142. Xef Val Xan Pro Pro NH$_2$ | 209. Xaa Val Xan Pro Pro Xgu |
| 143. Xbz Val Xan Pro Pro NH$_2$ | 210. Xaa Val Xan Pro Pro Xgs |
| 144. Xeg Val Xan Pro Pro NH$_2$ | 211. Xaa Val Xan Pro Pro Xgx |
| 145. Xca Val Xan Pro Pro NH$_2$ | 212. Xaa Val Xan Pro Pro Xha |
| 146. Xcb Val Xan Pro Pro NH$_2$ | 213. Xaa Val Xan Pro Pro Xhk |
| 147. Xcc Val Xan Pro Pro NH$_2$ | 214. Xaa Val Xan Pro Xek |
| 148. Xce Val Xan Pro Pro NH$_2$ | 215. Xaa Val Xan Pro Xen |
| 149. Xcg Val Xan Pro Pro NH$_2$ | 216. Xaa Val Xan Pro Xer |
| 150. Xch Val Xan Pro Pro NH$_2$ | 217. Xaa Val Xan Pro Xep |
| 151. Xci Val Xan Pro Pro NH$_2$ | 218. Xaa Val Xan Pro Xeq |
| 152. Xck Val Xan Pro Pro NH$_2$ | 219. Xaa Val Xan Pro Xer |
| 153. Xcl Val Xan Pro Pro NH$_2$ | 220. Xaa Val Xan Pro Xet |
| 154. Xcm Val Xan Pro Pro NH$_2$ | 221. Xaa Val Xan Pro Xeu |
| 155. Xcn Val Xan Pro Pro NH$_2$ | 222. Xaa Val Xan Pro Xes |
| 156. Xhn Val Xan Pro Pro NH$_2$ | 223. Xaa Val Xan Pro Xfa |
| 157. Xho Val Xan Pro Pro NH$_2$ | 224. Xaa Val Xan Pro Xfd |
| 158. Xhp Val Xan Pro Pro NH$_2$ | 225. Xaa Val Xan Pro Xfg |
| 159. Xhq Val Xan Pro Pro NH$_2$ | 225. Xaa Val Xan Pro Xfl |
| 160. Xaa Val Xan Pro Pro Val Xei | 227. Xaa Val Xan Pro Xfk |
| 161. Xaa Val Xan Pro Pro Val Xem | 228. Xaa Val Xan Pro Xfm |
| 162. Xaa Val Xan Pro Pro Val Xeo | 229. Xaa Val Xan Pro Xfn |
| 153. Xaa Val Xan Pro Pro Val Xep | 230. Xaa Val Xan Pro Xfo |
| 164. Xaa Val Xan Pro Pro Val Xeq | 231. Xaa Val Xan Pro Xfp |
| 165. Xaa Val Xan Pro Pro Val Xex | 232. Xaa Val Xan Pro Xfq |
| 166. Xaa Val Xan Pro Pro Val Xey | 233. Xaa Val Xan Pro Xfr |
| 167. Xaa Val Xan Pro Pro Val Xfb | 234. Xaa Val Xan Pro Xfy |
| 168. Xaa Val Xan Pro Pro Val Xfe | 235. Xaa Val Xan Pro Xgb |
| 169. Xaa Val Xan Pro Pro Val Xfh | 236. Xaa Val Xan Pro Xge |
| 170. Xaa Val Xan Pro Pro Val Xfu | 237. Xaa Val Xan Pro Xgk |
| 171. Xaa Val Xan Pro Pro Val Xfv | 238. Xaa Val Xan Pro Xgn |

239. Xaa Val Xan Pro Xhi
240. Xaa Val Xan Pro Xgo
241. Xaa Val Xan Pro Xgp
242. Xaa Val Xan Pro Xgq
243. Xaa Val Xan Pro Xgt
244. Xaa Val Xan Pro Xgw
245. Xaa Val Xan Pro Xgz
246. Xaa Val Xan Pro Xhm
247. Xaa Xco Pro Pro Val Phe $NH_2$
248. Xaa Xcp Pro Pro Val Phe $NH_2$
249. Xaa Xcq Pro Pro Val Phe $NH_2$
250. Xaa Xcr Pro Pro Val Phe $NH_2$
251. Xaa Xcs Pro Pro Val Phe $NH_2$
252. Xaa Xct Pro Pro Val Phe $NH_2$
253. Xaa Xcu Pro Pro Val Phe $NH_2$
254. Xaa Xcw Pro Pro Val Phe $NH_2$
255. Xaa Xcv Pro Pro Val Phe $NH_2$
256. Xaa Xcx Pro Pro Val Phe $NH_2$
257. Xaa Xcy Pro Pro Val Phe $NH_2$
258. Xaa Xda Pro Pro Val Phe $NH_2$
259. Xaa Xdb Pro Pro Val Phe $NH_2$
260. Xaa Xdc Pro Pro Val Phe $NH_2$
261. Xaa Xdd Pro Pro Val Phe $NH_2$
262. Xaa Xdf Pro Pro Val Phe $NH_2$
263. Xaa Xdg Pro Pro Val Phe $NH_2$
264. Xaa Xdh Pro Pro Val Phe $NH_2$
265. Xaa Xco Pro Pro Val $NH_2$
266. Xaa Xcp Pro Pro Val $NH_2$
267. Xaa Xcq Pro Pro Val $NH_2$
268. Xaa Xcr Pro Pro Val $NH_2$
269. Xaa Xcs Pro Pro Val $NH_2$
270. Xaa Xct Pro Pro Val $NH_2$
271. Xaa Xcu Pro Pro Val $NH_2$
272. Xaa Xcw Pro Pro Val $NH_2$
273. Xaa Xcv Pro Pro Val $NH_2$
274. Xaa Xcx Pro Pro Val $NH_2$
275. Xaa Xcy Pro Pro Val $NH_2$
276. Xaa Xcz Pro Pro Val $NH_2$
277. Xaa Xda Pro Pro Val $NH_2$
278. Xaa Xdb Pro Pro Val $NH_2$
279. Xaa Xdc Pro Pro Val $NH_2$
280. Xaa Xde Pro Pro Val $NH_2$
281. Xaa Xdf Pro Pro Val $NH_2$
282. Xaa Xdg Pro Pro Val $NH_2$
283. Xaa Xdh Pro Pro Val $NH_2$
284. Xaa Xco Pro Pro $NH_2$
285. Xaa Xcp Pro Pro $NH_2$
286. Xaa Xcq Pro Pro $NH_2$
287. Xaa Xcr Pro Pro $NH_2$
288. Xaa Xcs Pro Pro $NH_2$
289. Xaa Xct Pro Pro $NH_2$
290. Xaa Xcu Pro Pro $NH_2$
291. Xaa Xcw Pro Pro $NH_2$
292. Xaa Xcv Pro Pro $NH_2$
293. Xaa Xcx Pro Pro $NH_2$
294. Xaa Xcy Pro Pro $NH_2$
295. Xaa Xcz Pro Pro $NH_2$
296. Xaa Xda Pro Pro $NH_2$
297. Xaa Xdb Pro Pro $NH_2$
298. Xaa Xdc Pro Pro $NH_2$
299. Xaa Xdd Pro Pro $NH_2$
300. Xaa Xdf Pro Pro $NH_2$
301. Xaa Xdg Pro Pro $NH_2$
302. Xaa Xdh Pro Pro $NH_2$
303. Xds Xan Pro Pro Val Phe $NH_2$
304. Xdt Xan Pro Pro Val Phe $NH_2$
305. Xdu Xan Pro Pro Val Phe $NH_2$
306. Xdv Xan Pro Pro Val Phe $NH_2$
307. Xdw Xan Pro Pro Val Phe $NH_2$
308. Xdx Xan Pro Pro Val Phe $NH_2$
309. Xdy Xan Pro Pro Val Phe $NH_2$
310. Xdz Xan Pro Pro Val Phe $NH_2$
311. Xea Xan Pro Pro Val Phe $NH_2$
312. Xeb Xan Pro Pro Val Phe $NH_2$
313. Xec Xan Pro Pro Val Phe $NH_2$
314. Xds Xan Pro Pro Val $NH_2$
315. Xdt xan Pro Pro Val $NH_2$
316. Xdu Xan Pro Pro Val $NH_2$
317. Xdv Xan Pro Pro Val $NH_2$
318. Xdw Xan Pro Pro Val $NH_2$
319. Xdx Xan Pro Pro Val $NH_2$
320. Xdy Xan Pro Pro Val $NH_2$
321. Xdz Xan Pro Pro Val $NH_2$
322. Xea Xan Pro Pro Val $NH_2$
323. Xeb Xan Pro Pro Val $NH_2$
324. Xed Xan Pro Pro Val $NH_2$
325. Xds Xan Pro Pro $NH_2$
326. Xdt Xan Pro Pro $NH_2$
327. Xdu Xan Pro Pro $NH_2$
328. Xdv Xan Pro Pro $NH_2$
329. Xdw Xan Pro Pro $NH_2$
330. Xdx Xan Pro Pro $NH_2$
331. Xdy Xan Pro Pro $NH_2$
332. Xdz Xan Pro Pro $NH_2$
333. Xea Xan Pro Pro $NH_2$
334. Xeb Xan Pro Pro $NH_2$
335. Xec Xan Pro Pro $NH_2$
336. Xds Val Pro Pro Val Phe $NH_2$
337. Xds Val Pro Pro $NH_2$
338. Xdv Val Pro Pro $NH_2$
339. Xds Xan Pro Xfy
340. Xdv Xan Pro Xfy
341. Xaa Val Xhf Pro Pro Val Phe $NH_2$
342. Xaa Val Xhg Pro Pro Val Phe $NH_2$
343. Xaa Val Xhh Pro Pro Val Phe $NH_2$
344. Xaa Val Xhf Pro Pro Val $NH_2$
345. Xaa Val Xhg Pro Pro Val $NH_2$
346. Xaa Val Xhh Pro Pro Val $NH_2$
347. Xaa Val Xhf Pro Pro $NH_2$
348. Xaa Val Xhg Pro Pro $NH_2$
349. Xaa Val Xhh Pro Pro $NH_2$
350. Xaa Val Xhf Pro Xfy
351. Xaa Val Xhg Pro Xfy
352. Xaa Val Xhh Pro Xfy
353. Xaa Val Xhf Pro Xgb
354. Xaa Val Xhg Pro Xgb
355. Xaa Val Xhh Pro Xgb
356. Xed Val Xan Pro Xfy
357. Xby Val Xan Pro Xfy
358. Xby Val Xan Pro Xhi
359. Xef Val Xan Pro Xfy
360. Xef Val Xan Pro Xhi
361. Xca Val Xan Pro Xfy
362. Xca Val Xan Pro Xhi
363. Xaa Val Xan Pro Xdp Phe $NH_2$
364. Xaa Val Xan Pro Xdq Phe $NH_2$
365. Xaa Val Xan Pro Xdr Phe $NH_2$
366. Xaa Val Xan Pro Xdp $NH_2$
367. Xaa val Xan Pro Xdq $NH_2$
368. Xaa Val Xan Pro Xdr $NH_2$
369. Xaa Val Xan Pro Pro Xdi $NH_2$
370. Xaa Val Xan Pro Pro Xcs $NH_2$
371. Xaa Val Xan Pro Pro Xct $NH_2$
372. Xaa Val Xan Pro Pro Xcu $NH_2$ 373. Xaa Xcs Pro Pro Xdi NH₂
374. Xaa Xct Pro Pro Xdi NH₂
375. Xaa Xcs Pro Xdp Phe NH₂
376. Xaa Xct Pro Xdp Phe NH₂
377. Xaa Xcs Pro Xdp NH₂
378. Xaa Xct Pro Xdp NH₂
379. Xaa Xcs Pro Xdq NH₂
380. Xaa Xct Pro Xdq NH₂
381. Xaa Xcs Pro Xdr NH₂
382. Xaa Xct Pro Xdr NH₂
383. Xaa Val Xan Pro Pro Xdi NH₂
384. Xaa Val Xan Pro Pro Xdk NH₂
385. Xaa Val Xan Pro Pro Xdl NH₂
386. Xaa Val Xan Pro Pro Xdm NH₂
387. Xaa Val Xan Pro Pro Xdn NH₂
388. Xaa Val Xan Pro Pro Xdo NH₂
389. Xca Val Xan Pro Pro Phe Phe NH₂
390. Xby Val Xan Pro Pro Phe Phe NH₂
391. Xca Val Xan Pro Pro Phe Phe NH₂
392. Xef Val Xhf Pro Pro Xai Phe NH₂
393. Xef Val Xhf Pro Pro Xai Xah NH₂
394. Xef Val Xhf Pro Pro Xai Xag NH₂
395. Xef Val Xan Pro Xfy
396. Xef Val Xan Pro Xbg
397. Xef Val Xan Pro Xbh
398. Xef Val Xan Pro Xgn
399. Xca Xct Pro Xfy
400. Xaa Xai Xan Pro Pro Val Phe NH₂
401. Xaa Leu Xan Pro Pro Val Phe NH₂
402. Xaa Ile Xan Pro Pro Val Phe NH₂
403. Xaa Val Xan Pro Pro Xai Phe NH₂
404. Xaa Val Xan Pro Pro Leu Phe NH₂
405. Xaa Val Xan Pro Pro Ile Phe NH₂
406. Xaa Val Xan Pro Pro Val Dab NH₂
407. Xaa Val Xan Pro Pro Val Ala NH₂
408. Xaa Dab Xan Pro Pro Val Phe NH₂
409. Xaa Xab Xan Pro Pro Val NH₂
410. Xaa Dab Xan Pro Pro NH₂
411. Xht Val Xan Pro Pro Val Phe NH₂
412. Xhu Val Xan Pro Pro Val Phe NH₂
413. Xht Val Xan Pro Pro Val NH₂
413.(a). Xhu Val Xan Pro Pro Val NH₂
414. Xht Val Xan Pro Pro NH₂
415. Xhu Val Xan Pro Pro NH₂
416. Xaa Val Xhy Pro Pro Val Phe NH₂
417. Xaa Val Xhz Pro Pro Val Phe NH₂
418. Xaa Val Xhy Pro Pro Val NH₂
419. Xaa Val Xhz Pro Pro Val NH₂
420. Xaa Val Xhy Pro Pro NH₂
421. Xaa Leu Xhz Pro Pro NH₂
422. Xaa Val Xhy Xfy
423. Xaa Val Xhz Xfy
424. Xhv Val Xan Pro Pro Val Phe NH₂
425. Xhw Val Xan Pro Pro Val Phe NH₂
426. Xhx Val Xan Pro Pro Val Phe NH₂
427. Xhv Val Xan Pro Pro Val NH₂
428. Xhw Val Xan Pro Pro Val NH₂
429. Xhx Val Xan Pro Pro Val NH₂
430. Xhv Val Xan Pro Pro NH₂
431. Xhw Val Xan Pro Pro NH₂
432. Xhx Val Xan Pro Pro NH₂
433. Xaa Val Xan Pro Xia
434. Xaa Val Xan Pro Xib
435. Xaa Val Xan Pro Xic
436. Xaa Val Xan Pro Xid
437. Xaa Val Xan Pro Xie
438. Xby Val Xan Pro Xia
439. Xby Val Xan Pro Xib
440. Xby Val Xan Pro Xic
441. Xby Val Xan Pro Xid
442. Xby Val Xan Pro Xie
443. Xca Val Xan Pro Xia
444. Xca Val Xan Pro Xib
445. Xca Val Xan Pro Xic
446. Xca Val Xan Pro Xid
447. Xca Val Xan Pro Xie
448. Xed Val Xan Pro Xia
449. Xed Val Xan Pro Xib
450. Xed Val Xan Pro Xic
451. Xed Val Xan Pro Xld
452. Xed Val Xan Pro Xie
453. Xby Leu Xan Pro Xia
454. Xby Leu Xan Pro Xib
455. Xby Ile Xan Pro Xic
455. Xby Ile Xan Pro Xid
457. Xby Leu Xan Pro Xie
458. Xca Leu Xan Pro Xia
459. Xca Val Xao Pro Xib
460. Xca Val Xao Pro Xic
461. Xat Val Xhf Pro Xak Leu Phe NH₂
462. Xat Val Xhf Pro Xhr Leu Phe NH₂
463. Xed Val Xhf Pro Xak Leu Phe NH₂
464. Xed Val Xhf Pro Xhr Leu Phe NH₂
465. Xat Val Xhf Pro Xak Val NH₂
466. xat Val Xhf Pro Xhr Val NH₂
467. Xed Val Xhf Pro Xak Val NH₂
468. Xed Val Xhf Pro Xhr Val NH₂
469. Xat Val Xhf Pro Xak NH₂
470. Xat Val Xhf Pro Xhr NH₂
471. Xed Val Xhf Pro Xak NH₂
472. Xat Val Xhf Pro Xia
473. Xat Val Xhf Pro Xib
474. Xed Val Xhf Pro Xic
475. Xed Val Xhf Pro Xid
476. Xat Val Xhf Pro Xie
477. Xat Val Xhf Pro Xhs NH₂
478. Xed Val Xhf Pro Xhs NH₂
479. Xat Val Xhf Pro Xak Xfz
480. Xat Val Xhf Pro Xhr Xfz
481. Xed Val Xhf Pro Xak Xfz
482. Xed Val Xhf Pro Xhr Xfz
483. Xat Val Xhf Pro Xak Xbw
484. Xat Val Xhf Pro Xhr Xbw
485. Xed Val Xhf Pro Xak Xbw
486. Xed Val Xhf Pro Xhr Xbw
487. Xat Val Xhf Pro Xak Xer
488. Xat Val Xhf Pro Xhr Xer
489. Xed Val Xhf Pro Xak Xer
490. Xed Val Xhf Pro Xhr Xer
491. Xat Val Xhf Pro Xak Xgi
492. Xat Val Xhf Pro Xhr Xgi
493. Xed Val Xhf Pro Xak Xgi
494. Xed Val Xhf Pro Xhr Xgi
495. Xat Val Xhf Pro Xak Xif
496. Xat Val Xhf Pro Xhr Xif
497. Xed Val Xhf Pro Xak Xif
498. Xed Val Xhf Pro Xhr Xif
499. Xat Val Xhf Pro Xak Xig
500. Xat Val Xhf Pro Xhr Xig
501. Xed Val Xhf Pro Xak Xig
502. Xed Val Xhf Pro Xhr Xig
503. Xaa Val Xan Pro Pro Xlf
504. Xaa Val Xan Pro Xig
505. Xca Val Xan Pro Pro Xif 506. Xca Val Xan Pro Xlg
507. Xby Val Xan Pro Pro Xif
508. Xby Val Xan Pro Xig
509. Xed Val Xan Pro Pro Xif
510. Xed Val Xan Pro Xig
511. Xaa Leu Xan Pro Pro Xif
512. Xaa Leu Xan Pro Xig
513. Xca Leu Xan Pro Pro Xif
514. Xca Leu Xan Pro Xig
515. Xby Leu Xan Pro Pro Xif
516. Xby Leu Xan Pro Xig
517. Xed Leu Xan Pro Pro Xif
518. Xed Leu Xan Pro Xig
519. Xaa Lys Xan Pro Pro Val Phe $NH_2$
520. Xaa Lys Xan Pro Pro Val $NH_2$
521. Xaa Lys Xan Pro Pro $NH_2$
522. Xaa Lys Xan Pro Xfy
523. Xaa Xih Xan Pro Pro Val $NH_2$
524. Xaa Xih Xan Pro Pro $NH_2$
525. Xaa Xih Xan Pro Pro Val Phe $NH_2$
525. Xaa Val Xii Pro Pro Val Phe $NH_2$
527. Xaa Val Xii Pro Pro Val $NH_2$
528. Xaa Val Xii Pro Pro $NH_2$
529. Xaa Val Xan Pro Pro Val Lys $NH_2$
530. Xaa Val Xan Pro Xik
531. Xaa Val Xan Pro Pro Xil $NH_2$
532. Xaa Val Xbu
533. Xby Val Xbu
534. Xca Val Xbu
535. Xaa Val Xbv
536. Xby Val Xbv
537. Xca Val Xbv
538. Xaa Val Xan Pro Pro Xab
539. Xaa Val Xan Xab
540. Xim Val Xan Pro Pro Val Phe $NH_2$
541. Xin Val Xan Pro Pro Val Phe $NH_2$
542. Xio Val Xan Pro Pro Val Phe $NH_2$
543. Xip Val Xan Pro Pro Val Phe $NH_2$
544. Xiq Val Xan Pro Pro Val Phe $NH_2$
545. Xkd Val Xan Pro Pro Val Phe $NH_2$
546. Xim Val Xan Pro Pro Val $NH_2$
547. Xin Val Xan Pro Pro Val $NH_2$
548. Xio Val Xan Pro Pro Val $NH_2$
549. Xip Val Xan Pro Pro Val $NH_2$
550. Xiq Val Xan Pro Pro Val $NH_2$
551. Xkd Val Xan Pro Pro Val $NH_2$
552. Xim Val Xan Pro Pro $NH_2$
553. Xin Val Xan Pro Pro $NH_2$
554. Xio Val Xan Pro Pro $NH_2$
555. Xip Val Xan Pro Pro $NH_2$
556. Xiq Val Xan Pro Pro $NH_2$
557. Xkd Val Xan Pro Pro $NH_2$
558. Xaa Val Xan Pro Pro Val Xir
559. Xaa Val Xan Pro Pro Val Xis
560. Xaa Val Xan Pro Pro Val Xit
561. Xaa Val Xan Pro Pro Val Xiu
562. Xaa Val Xan Pro Pro Xiv
563. Xaa Val Xan Pro Pro Xiw
564. Xaa Val Xan Pro Pro Xiy
565. Xaa Val Xan Pro Pro Xix
566. Xaa Val Xan Pro Xiz
567. Xaa Val Xan Pro Xka
568. Xaa Val Xan Pro Xkb
569. Xaa Val Xan Pro Xkc
570. Xke Val Xan Pro Pro Val Phe $NH_2$
571. Xkf Val Xan Pro Pro Val Phe $NH_2$
572. Xkg Val Xan Pro Pro Val Phe $NH_2$
573. Xkh Val Xan Pro Pro Val Phe $NH_2$
574. Xke Val Xan Pro Pro Val $NH_2$
575. Xkf Val Xan Pro Pro Val $NH_2$
576. Xkg Val Xan Pro Pro Val $NH_2$
577. Xkh Val Xan Pro Pro Val $NH_2$
578. Xke Val Xan Pro Pro $NH_2$
579. Xkf Val Xan Pro Pro $NH_2$
580. Xkg Val Xan Pro Pro $NH_2$
581. Xkh Val Xan Pro Pro $NH_2$
582. Xaa Xcz Pro Pro Val Phe $NH_2$
583. Xed Val Xhf Pro Xhr $NH_2$
584. Val Val Xan Pro Pro Val Phe
585. Xaa Val Xan Pro Pro Val
586. Xaa Val Xki Pro Pro Val Phe $NH_2$
587. Xaa Val Xan Pro Pro Val Xhz $NH_2$
588. Xaa Val Xan Pro Pro Val Xah $NH_2$
589. Xaa Val Xan Pro Pro Val Tyr $NH_2$
590. Xaa Val Xan Pro Pro Phe Phe $NH_2$
591. Xaa Val Xan Pro Pro Val Xkj $NH_2$
592. Xaa Val Xan Xbb
593. Xaa Val Xan Pro Pro Xab
594. Xaa Val Xan Xfp
595. Xaa Val Xan Xbg
596. Xaa Val Xan Xbx
597. Xaa Val Xan Pro Xbg
598. Xaa Val Xan Pro Pro Ile $NH_2$
599. Xaa Val Xan Pro Pro Leu $NH_2$
600. Xaa Val Xan Pro Pro Xlv $NH_2$
601. Xaa Val Xan Xfo
602. Xaa Val Xan Pro Pro Xlw Phe $NH_2$
603. Xaa Val Xan Pro Pro Xlx Phe $NH_2$
604. Xaa Val Xan Pro Pro Val Xlw $NH_2$
605. Xaa Val Xan Pro Xkr
606. Xar Val Xan Pro Xfy
607. Xat Xai Xan Pro Xfy
608. Xaa Val Xan Pro Pro Val Xlv $NH_2$
609. Xaa Val Xan Pro Xkc
610. Xaa Val Xan Pro Xbm
611. Xaa Val Xan Pro Xka
612. Xaa Val Xan Pro Xks
613. Xaa Val Xan Pro Xiz
614. Xaa Val Xan Pro Xbk
615. Xaa Val Xan Pro Xen
616. Xaa Val Xan Pro Xhi
617. Xaa Val Xan Pro Xbh
618. Xaa Val Xan Pro Xfd
619. Xaa Val Xan Pro Xgn
620. Xbo Val Xan Pro Xfy
621. Xat Val Xan Pro Xfy
622. Xas Val Xan Pro Xfy
623. Xaa Val Xam Pro Xfy
624. Xcl Val Xan Pro Xfy
625. Xci Val Xan Pro Xfy
626. Xaa Val Xhz Pro Xfy
627. Xaa Val Xan Pro Xkt
628. Xaa Val Xan Pro Xku
629. Xaa Val Xan Pro Xkv
630. Xaa Val Xan Pro Xkw
631. Xaa Val Xhh Pro Xfy
632. Xaa Ile Xan Pro Xfy
633. Xaa Val Xan Xak Xfy
634. Xaa Val Xan Pro Xkb
635. Xat Val Xan Pro Xbg
636. Xar Val Xan Pro Xbg
637. Xar Val Xam Pro Xfy
638. Xaa Val Xan Pro Pro Xga
639. Xaa Val Xan Pro Xkx 640. Xaa Val Xan Pro Pro Leu Phe NH₂
641. Xaa Val Xan Pro Pro Ile Phe NH₂
642. Xaa Val Xan Pro Xky
643. Xaa Val Xan Pro Xkz
644. Xaa Val Xan Pro Xfr
645. Xaa Val Xam Pro Pro NH₂
646. Xaa Val Xan Pro Xla
647. Xaa Val Xan Pro Xlb
648. Xaa Val Xan Pro Xlc
649. Xaa Val Xan Pro Xld
650. Xaa Val Xan Pro Xkk
651. Xaa Val Xan Pro Xek
652. Xaa Val Xan Pro Xle
653. Xaa Val Xan Pro Xlf
654. Xaa Val Xan Pro Xlg
655. Xaa Val Xan Pro Xkl
656. Xaa Val Xan Pro Xlh
657. Xkm Val Xan Pro Xfy
658. Xaa Val Xan Pro Xli
659. Xaa Val Xan Pro Xlk
660. Xkn Val Xan Pro Xfy
661. Xaa Val Xan Pro Xll
662. Xaa Val Xan Pro Xlm
663. Xaa Val Xan Pro Xfk
664. Xaa Xma Xan Pro Xfy
665. Xaa Val Xhg Pro Xfy
666. Xaa Val Xhy Pro Xfy
667. Xaa Val Xan Pro Xln
668. Xaa Xai Xan Pro Xfy
669. Xaa Val Xao Pro Xfy
670. Xaa Val Xan Pro Xlo
671. Xaa Val Xan Pro Xko
672. Xaa Val Xan Pro Xkp
673. Xaa Val Xan Pro Xlp
674. Xaa Val Xan Pro Xlq
675. Xaa Val Xan Pro Pro Xlr
676. Xaa Val Xhf Pro Xfy
677. Xaa Val Xan Pro Xls
678. Xaa Val Xan Pro Xlt
679. Xby Val Xan Pro Xfy
680. Xkq Val Xan Pro Xfy
681. Xaa Val Xan Pro Xlu Examples for the MS-characterization of the synthesized novel compounds are given in the following table.

| EXAMPLE [No.] | Fast atom bombardment MS analysis. [Mol.-Weight (measured)] |
|---|---|
| 3. | 798 |
| 16. | 810 |
| 19. | 812 |
| 20. | 812 |
| 23. | 812 |
| 25. | 812 |
| 26. | 812 |
| 28. | 811 |
| 30. | 825 |
| 33. | 881 |
| 34. | 845 |
| 37. | 649 |
| 38. | 737 |
| 50. | 550 |
| 51. | 551 |
| 52. | 731 |
| 56. | 550 |
| 65. | 566 |
| 66. | 566 |
| 87. | 635 |
| 93. | 704 |
| 101. | 853 |
| 204. | 740 |
| 214. | 619 |
| 215. | 845 |
| 227. | 649 |
| 230. | 691 |
| 233. | 717 |
| 234. | 641 |
| 239. | 579 |
| 246. | 595 |
| 347. | 566 |
| 349. | 566 |
| 351. | 669 |
| 352. | 656 |
| 357. | 669 |
| 403. | 811 |
| 404. | 812 |
| 405. | 812 |
| 597. | 635 |
| 598. | 665 |
| 699. | 665 |
| 600. | 749 |
| 601. | 594 |
| 602. | 852 |
| 603. | 826 |
| 604. | 804 |
| 605. | 677 |
| 606. | 655 |
| 607. | 670 |
| 608. | 848 |
| 609. | 608 |
| 610. | 627 |
| 611. | 565 |
| 612. | 633 |
| 613. | 642 |
| 614. | 642 |
| 615. | 731 |
| 616. | 657 |
| 617. | 647 |
| 618. | 648 |
| 619. | 663 |
| 620. | 669 |
| 621. | 655 |
| 622. | 655 |
| 623. | 655 |
| 624. | 681 |
| 625. | 667 |
| 626. | 689 |
| 627. | 565 |
| 628. | 579 |
| 629. | 593 |
| 630. | 594 |
| 631. | 659 |
| 632. | 655 |
| 633. | 655 |
| 634. | 580 |
| 635. | 648 |
| 636. | 648 |
| 637. | 669 |
| 638. | 788 |
| 639. | 647 |
| 640. | 812 |
| 641. | 812 |
| 642. | 668 |
| 643. | 709 |
| 644. | 717 |
| 645. | 566 |
| 646. | 684 |
| 647. | 657 |
| 648. | 684 |
| 649. | 634 |
| 650. | 630 |
| 651. | 619 |
| 652. | 699 |
| 653. | 608 |
| 654. | 655 |
| 655. | 680 |
| 656. | 590 |

-continued

| EXAMPLE [No.] | Fast atom bombardment MS analysis. [Mol.-Weight (measured)] |
|---|---|
| 657. | 670 |
| 658. | 655 |
| 659. | 669 |
| 660. | 627 |
| 661. | 607 |
| 662. | 621 |
| 663. | 649 |
| 664. | 627 |
| 665. | 669 |
| 666. | 695 |
| 667. | 628 |
| 668. | 655 |
| 669. | 655 |
| 670. | 607 |
| 671. | 646 |
| 672. | 660 |
| 673. | 685 |
| 674. | 628 |
| 675. | 754 |
| 676. | 656 |
| 677. | 635 |
| 678. | 621 |
| 679. | 669 |
| 680. | 656 |
| 681. | 667 |

TABLE I

Sequence Identification of Compounds Prepared According to Examples 1 and 2

| Compound Number(s) | Sequence ID Number |
|---|---|
| 3, 9, 26–28, 30–33, 35, 36, 95–117, 341–343, 416, 417, 424–426, 526, 540–545, 570–573, 586 | 1 |
| 38, 39, 52, 86–91, 93, 214–246, 350–362, 366–368, 395–398, 433–452, 459, 460, 469–478, 504, 506, 508, 510, 530, 566–569, 583, 597, 606, 607, 609–611, 613–626, 631, 633–637, 644, 650, 651, 654, 655, 657, 660, 663, 665, 666, 669, 671, 672, 676, 679, 680 605, 612, 627, 628–630, 639, 642, 643, 645–649, 652, 653, 656, 658, 659, 661, 662, 667, 670, 673, 674, 677, 678, 681 | 2 |
| 4–7, 10, 11, 160–188, 406, 558–561, 587, 588, 591, 604, 608 | 3 |
| 8 | 4 |
| 12 | 5 |
| 13, 392, 403, 602, 603 | 6 |
| 14, 641 | 7 |
| 15, 16, 29 | 8 |
| 17, 18 | 9 |
| 19, 20 | 10 |
| 21, 22, 247–264, 303–313, 582 | 11 |
| 23, 402 | 12 |
| 24, 400 | 13 |
| 25, 401 | 14 |
| 34, 590 | 15 |
| 37, 118–138, 344–346, 585 | 16 |
| 40, 45, 189–213, 369-372, 383–388, 503, 505, 507, 509, 531, 538, 563–565, 593, 600, 638, 675 | 17 |
| 41–43, 48, 49, 527 | 18 |
| 44 | 19 |
| 46, 50, 51, 62–65, 70, 139–159, 347–349 414, 415, 420, 421, 430–432, 528, 552–557, 578–581 | 20 |
| 47 | 21 |
| 53–61, 78, 422, 423, 539, 592, 594–596 601 | 22 |
| 66, 67, 94, 410, 524 | 23 |

TABLE I-continued

Sequence Identification of Compounds Prepared According to Examples 1 and 2

| Compound Number(s) | Sequence ID Number |
|---|---|
| 68, 69, 284–302, 325–335 | 24 |
| 73, 83–85 | 25 |
| 92, 664, 668 | 26 |
| 265–283, 314–324 | 27 |
| 336 | 28 |
| 337, 338 | 29 |
| 339, 340, 377–382, 399 | 30 |
| 363–365 | 31 |
| 373, 374 | 32 |
| 375, 376 | 33 |
| 389–391 | 34 |
| 393, 394 | 35 |
| 404, 640 | 36 |
| 405 | 37 |
| 407 | 38 |
| 408 | 39 |
| 409 | 40 |
| 411, 412, 418, 419, 427–429, 546–551, 574–577 | 41 |
| 413, 413(a), 453, 454, 457, 458, 512 514, 516, 518 | 42 |
| 455, 456, 632 | 43 |
| 465–468 | 44 |
| 461–464 | 45 |
| 479–502 | 46 |
| 515, 517 | 47 |
| 513 | 48 |
| 519 | 49 |
| 520 | 50 |
| 521 | 51 |
| 522 | 52 |
| 523 | 53 |
| 525 | 54 |
| 529 | 55 |
| 584 | 56 |
| 589 | 57 |
| 598 | 58 |
| 599 | 59 |

The symbols Xaa ... in the summary have the following meanings:

Xaa: N,N-Dimethylvaline

Xab: 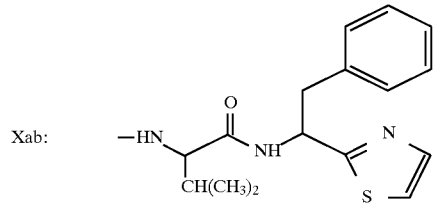

Xac: 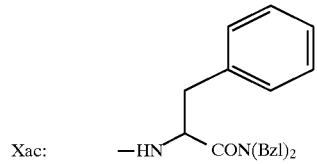

Xad: 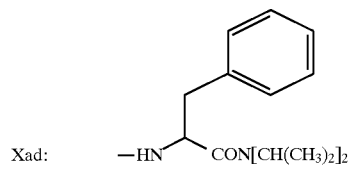

| | |
|---|---|
| Xae: | 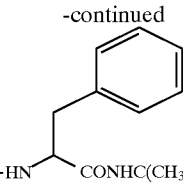 |
| Xaf: | 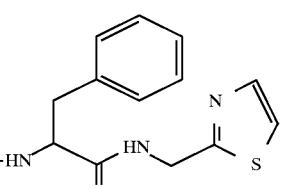 |
| Xag: | Tetrahydroisoquinoline carboxylic acid |
| Xah: | 1-Aminoindane-1-carboxylic acid |
| Xai: | tert-Leucine or 2-tert-butylglycine |
| Xak: | Homoproline or pipecolic acid |
| Xal: | 1-aminopentane-1-carboxylic acid |
| Xam: | N-Methylisoleucine |
| Xan: | N-Methylvaline |
| Xao: | N-Methylleucine |
| Xan: | N-Methylvaline |
| Xao: | N-Methylleucine |
| Xap: | 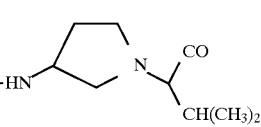 |
| Xaq: | 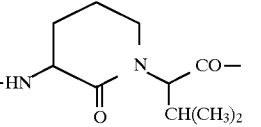 |
| Xar: | N-N-Dimethylisoleucine |
| Xas: | N,N-Dimethylleucine |
| Xat: | N,N-Dimethyl-tert-leucine |
| Xau: | N,N-Dimethyl-3-tert-butylalanin |
| Xav: | N-Acetyl-N-methylvaline |
| Xaw: | N-Methyl-N-benzylvaline |
| Xax: | N,N-Dibutylvaline |
| Xaz: | 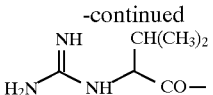 |
| Xba: | N-Benzylvaline |
| Xbb: | 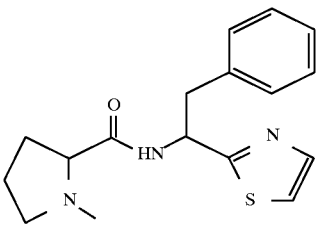 |
| Xbc: | 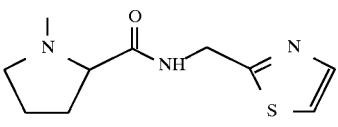 |
| Xbd: | 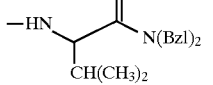 |
| Xbe: | 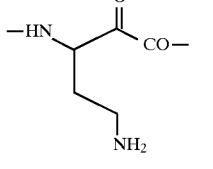 |
| Xbf: | 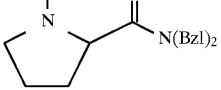 |
| Xbg: | 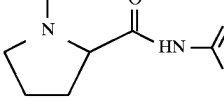 |
| Xbh: | 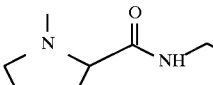 |
| Xbi: | 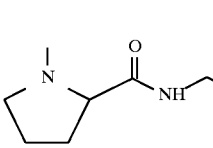 |
| Xbk: | 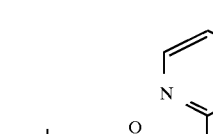 |

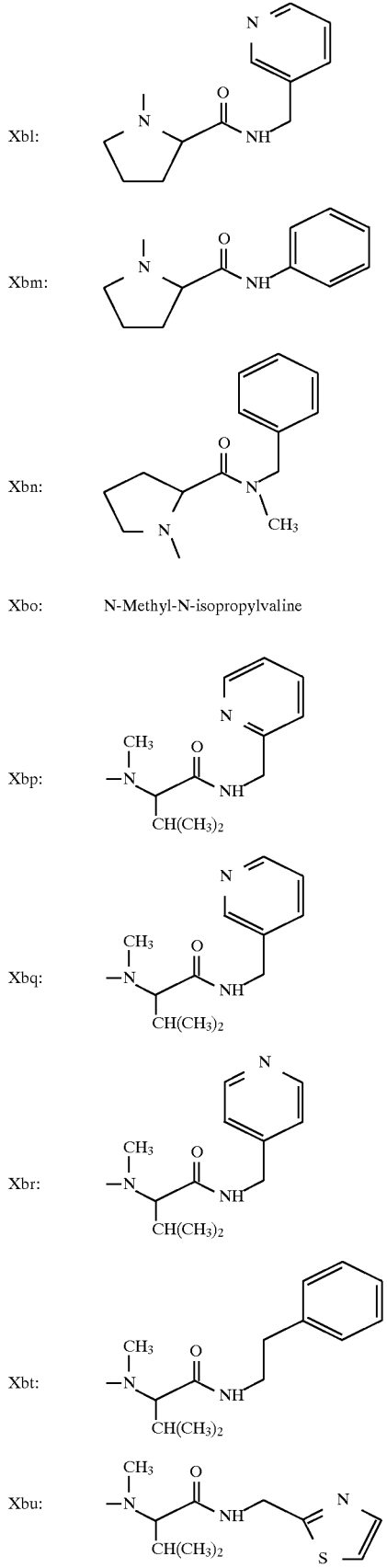
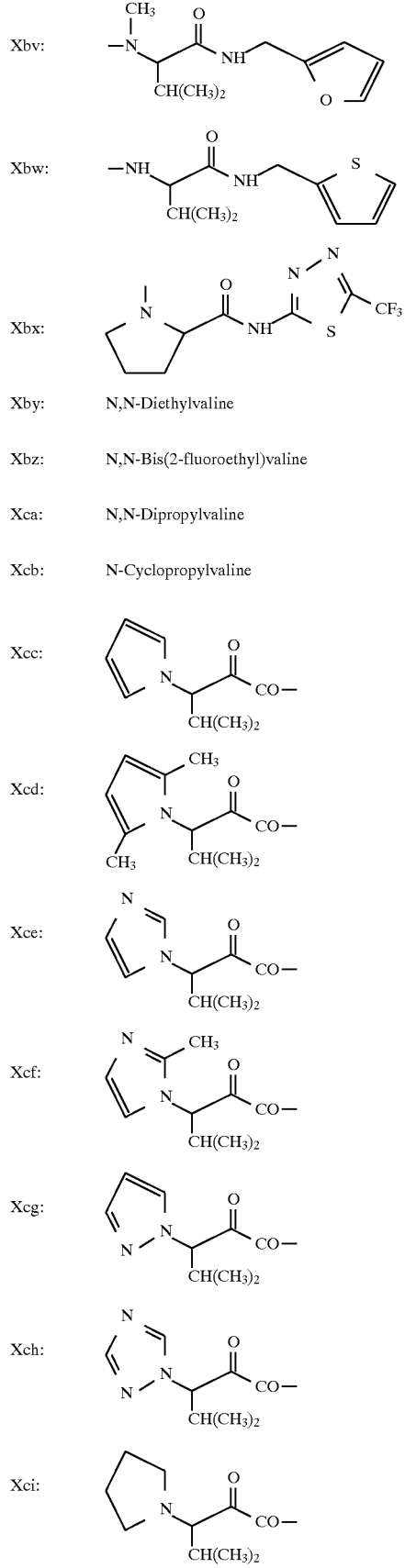
Xbo: N-Methyl-N-isopropylvaline
Xby: N,N-Diethylvaline
Xbz: N,N-Bis(2-fluoroethyl)valine
Xca: N,N-Dipropylvaline
Xcb: N-Cyclopropylvaline

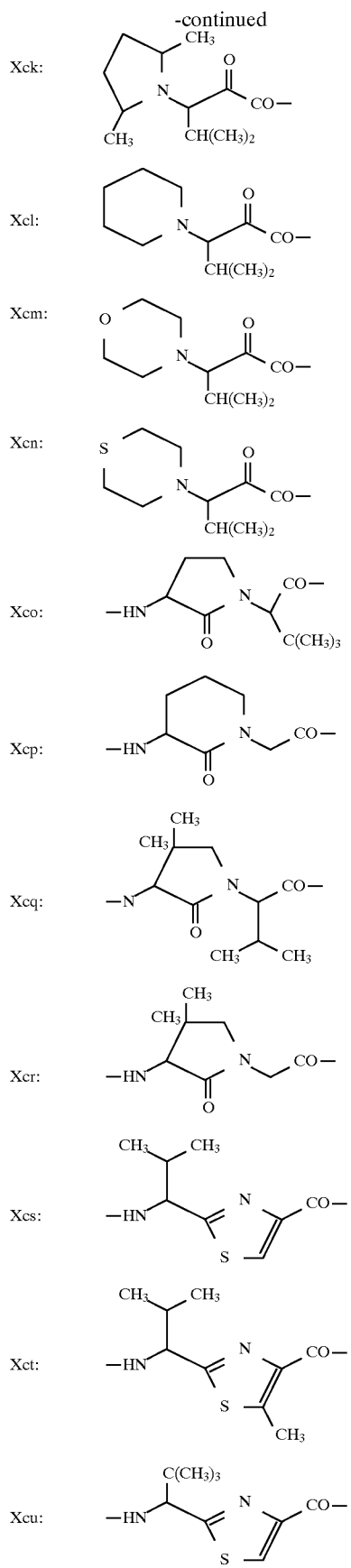
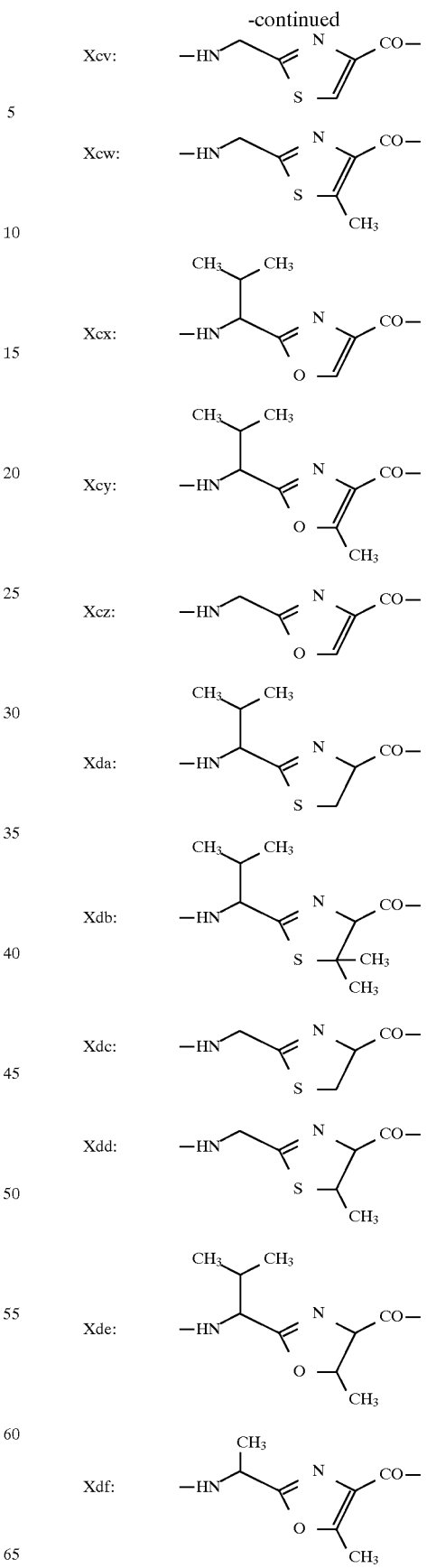

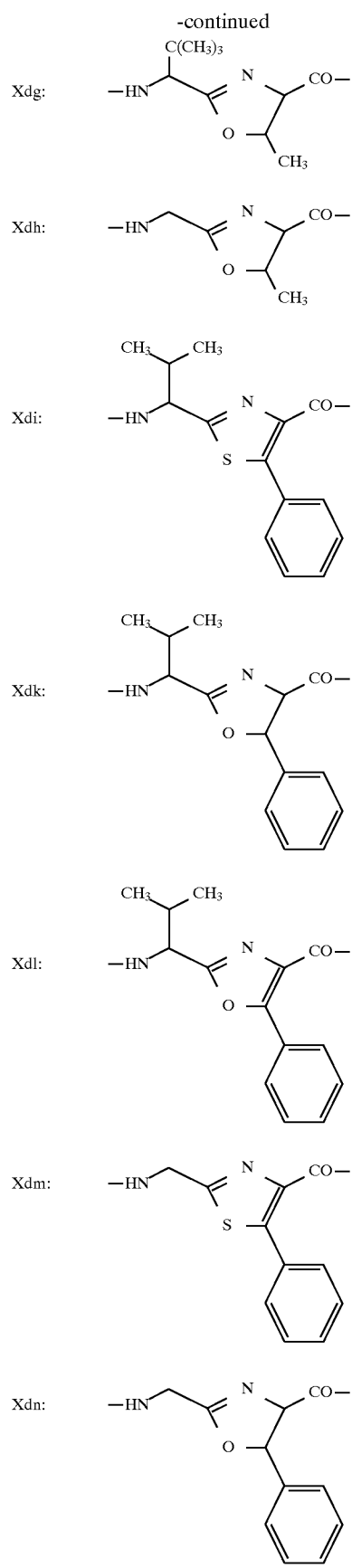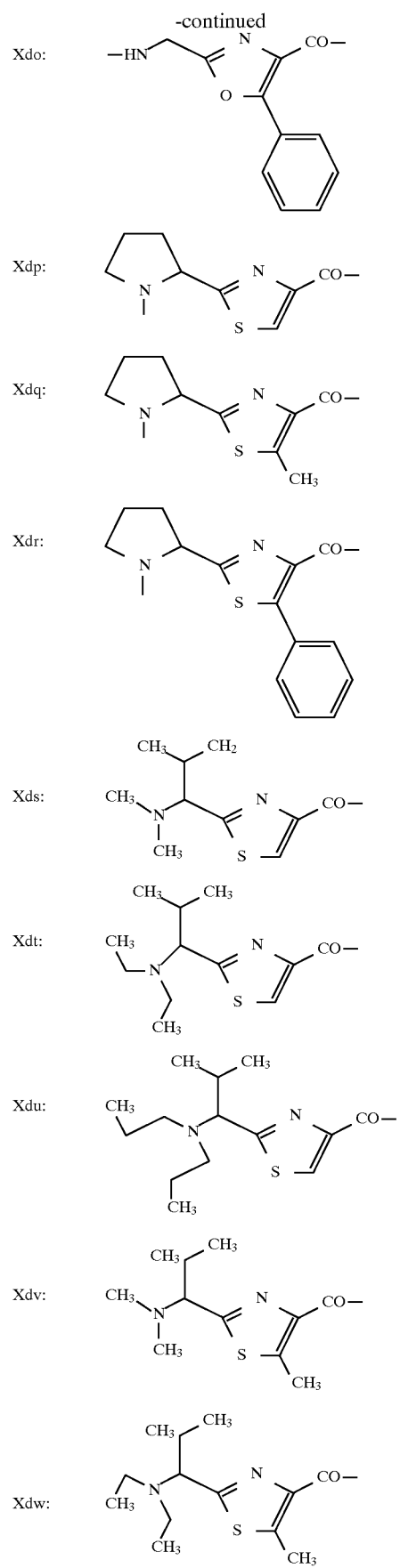

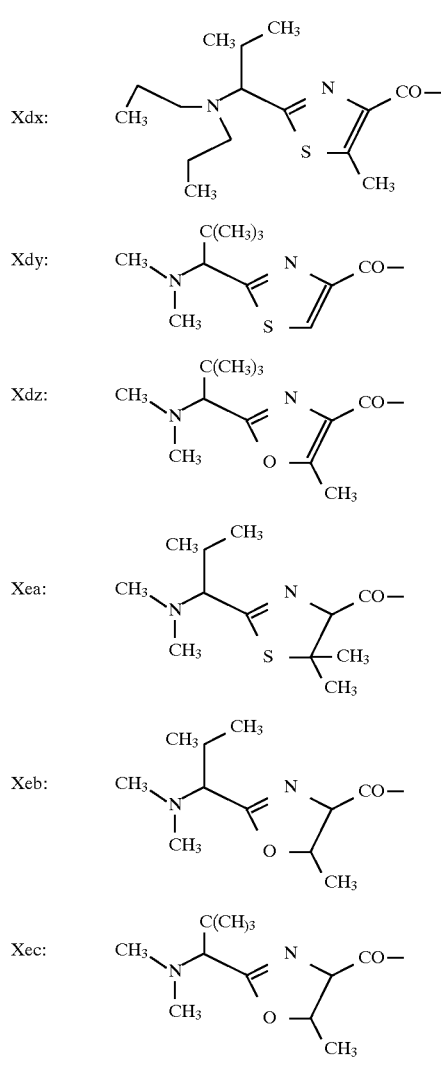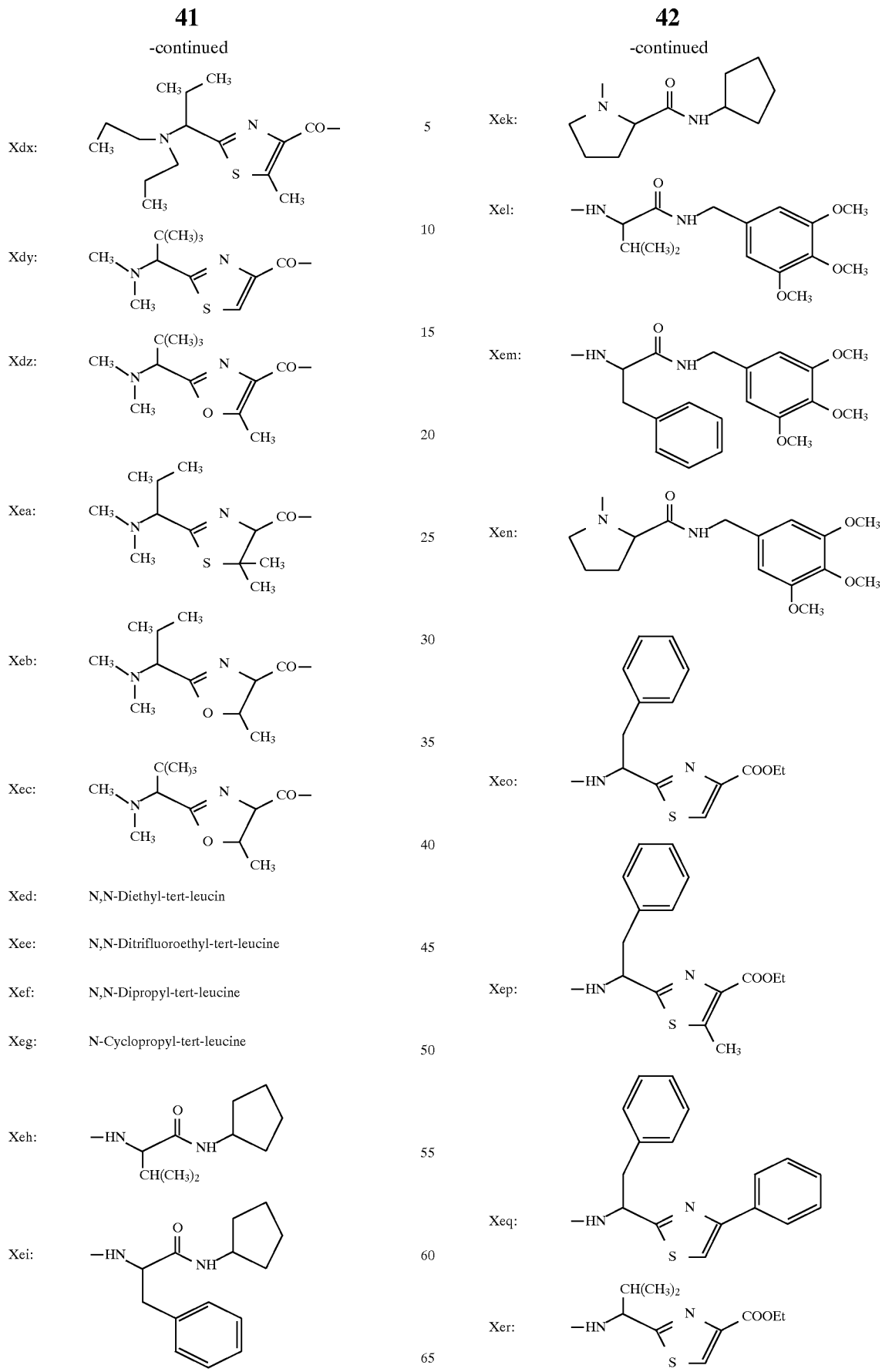
Xed: N,N-Diethyl-tert-leucin
Xee: N,N-Ditrifluoroethyl-tert-leucine
Xef: N,N-Dipropyl-tert-leucine
Xeg: N-Cyclopropyl-tert-leucine Xes: 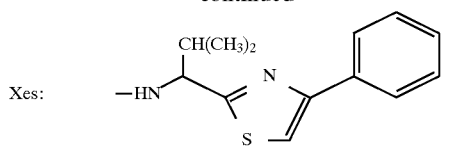
Xet: 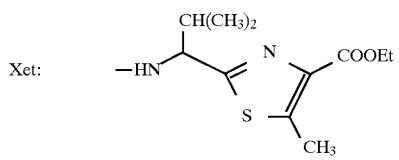
Xeu: 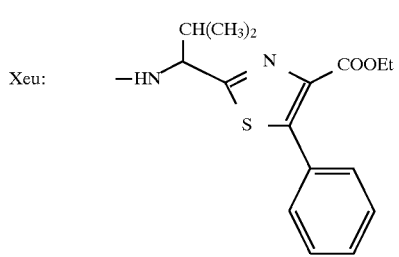
Xev: 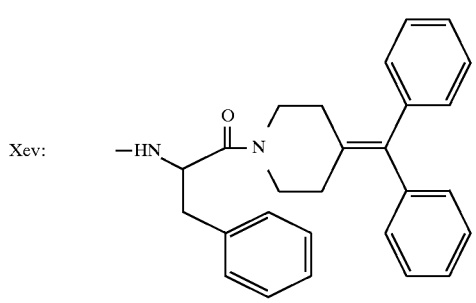
Xew: 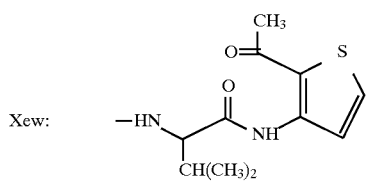
Xex: 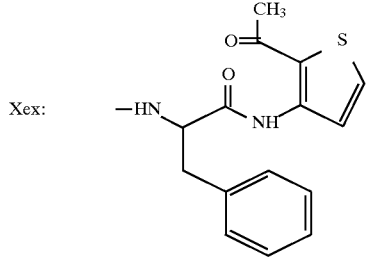
Xey: 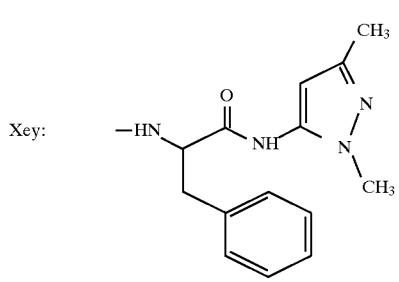
Xez: 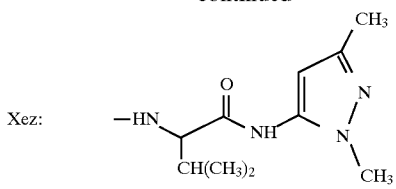
Xfa: 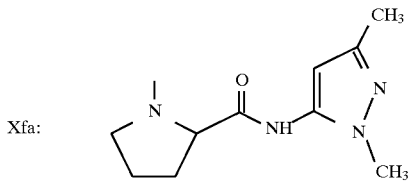
Xfb: 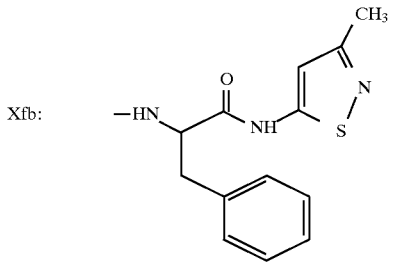
Xfc: 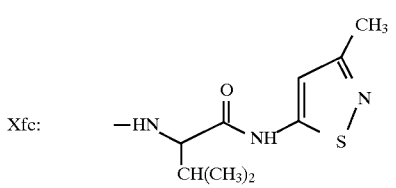
Xfd: 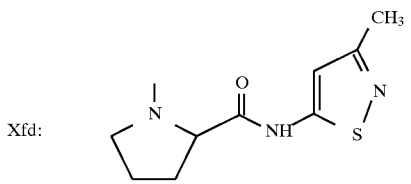
Xfe: 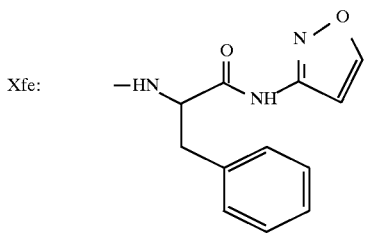
Xff: 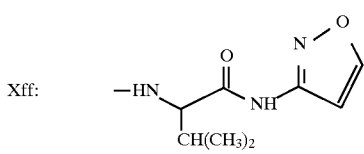
Xfg: 

Xfh: 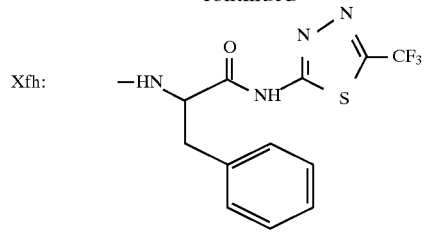
Xfi: 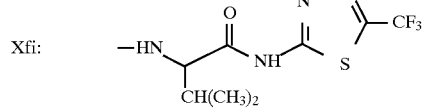
Xfk: 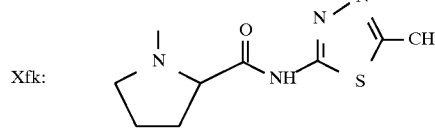
Xfl: 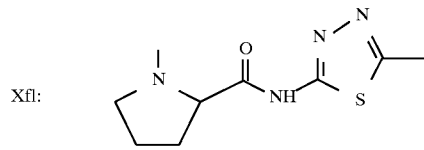
Xfm: 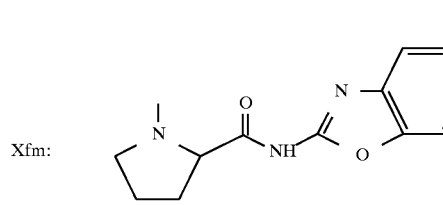
Xfn: 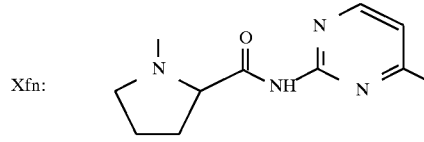
Xfo: 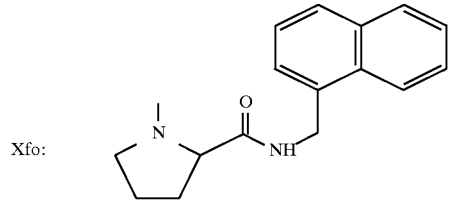
Xfp: 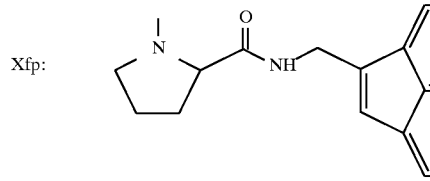
Xfq: 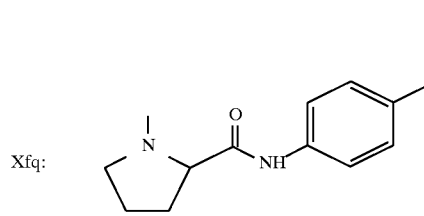
Xfr: 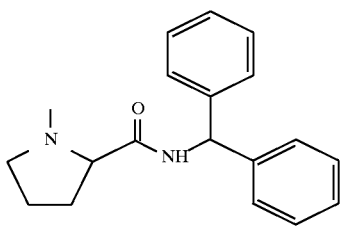
Xfs: 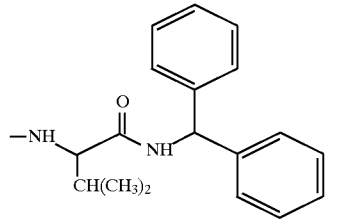
Xft: 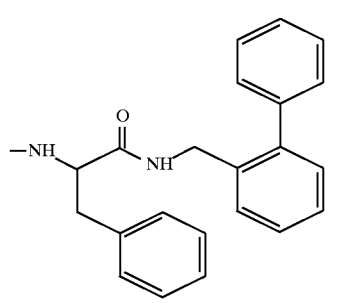
Xfu: 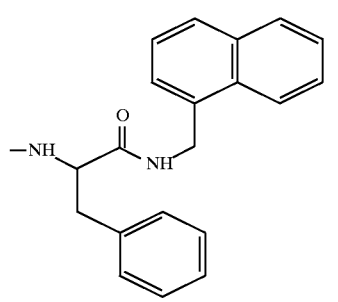
Xfv: 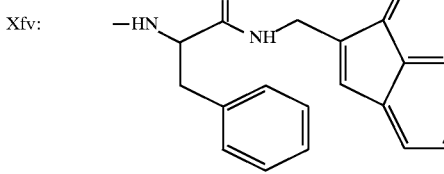
Xfw: 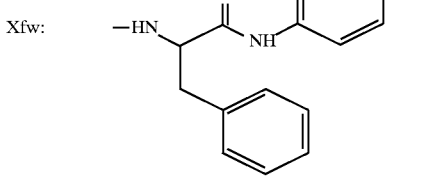

Xfx: 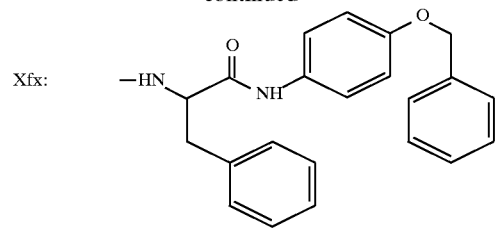
Xfy: 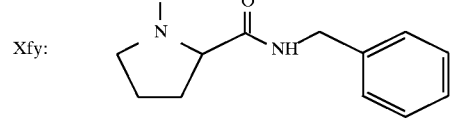
Xfz: 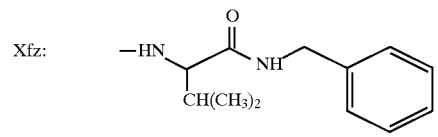
Xga: 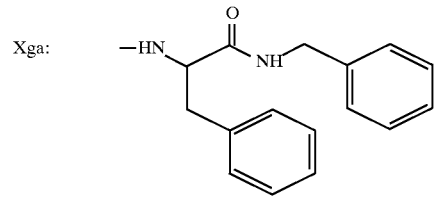
Xgb: 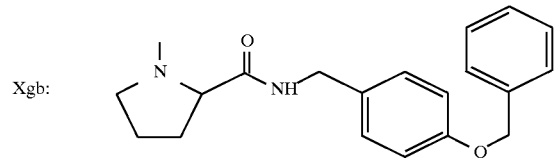
Xgc: 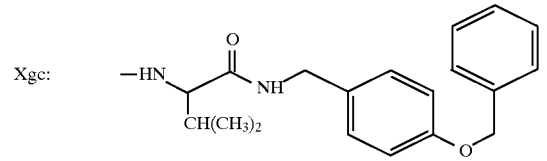
Xgd: 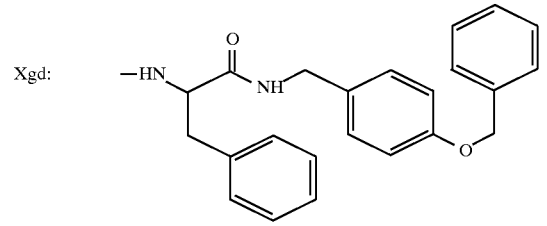
Xge: 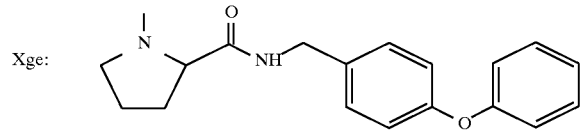
Xgf: 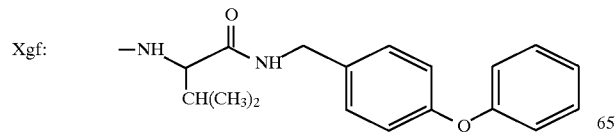
Xgg: 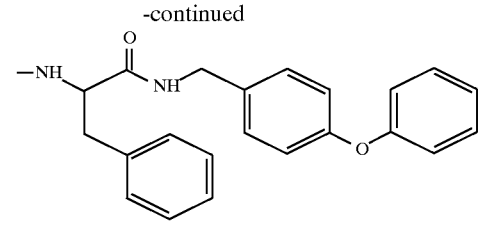
Xgh: 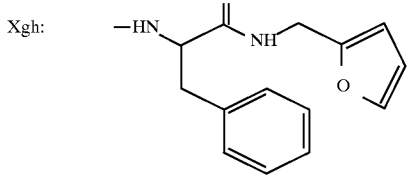
Xgi: 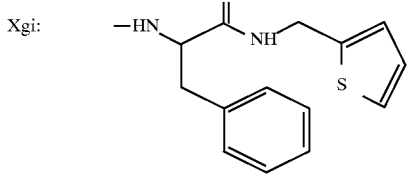
Xgk: 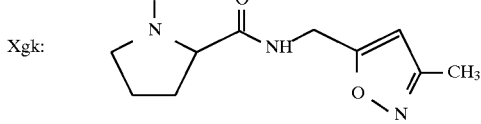
Xgl: 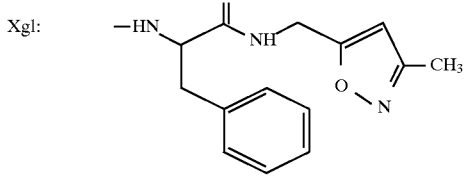
Xgm: 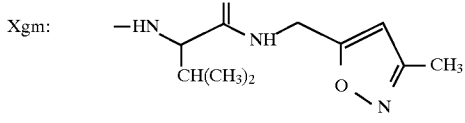
Xgn: 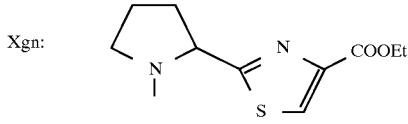
Xgo: 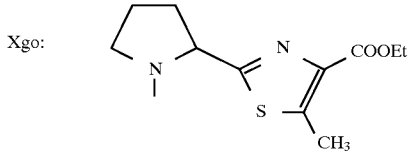
Xgp: 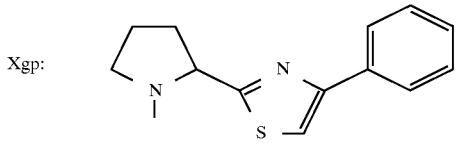

Xgq: 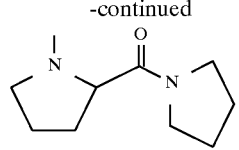
Xgr: 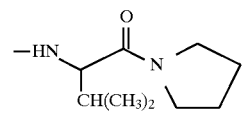
Xgs: 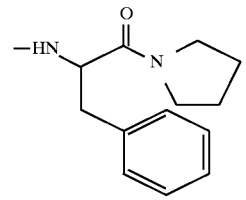
Xgt: 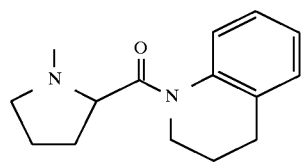
Xgu: 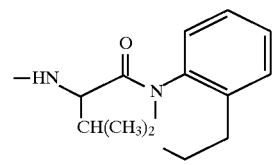
Xgv: 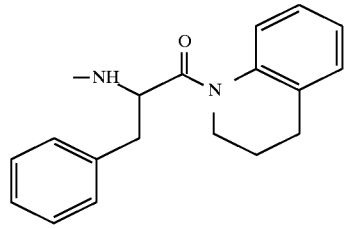
Xgw: 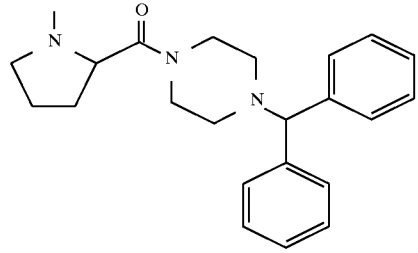
Xgx: 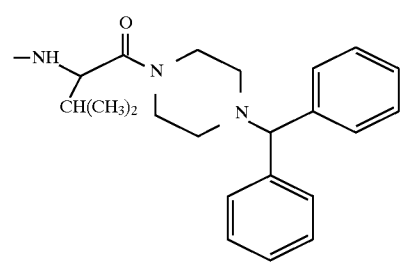
Xgy: 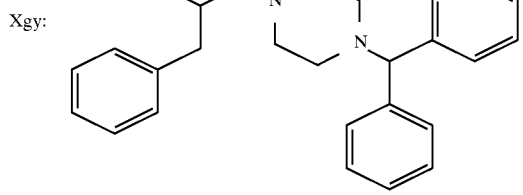
Xgz: 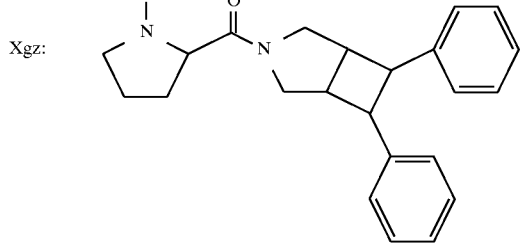
Xha: 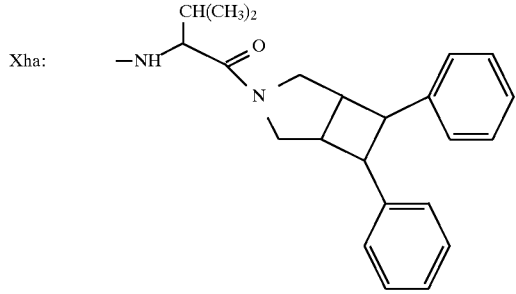
Xhb: 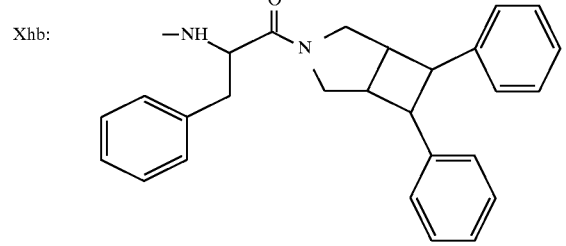
Xhc: 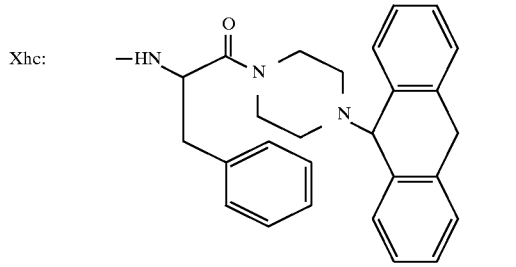
Xhd: 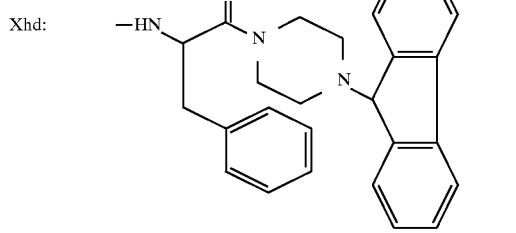

Xhe: 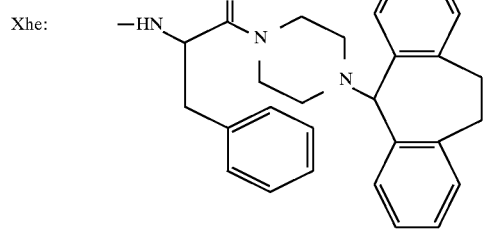

Xhf: N-Methyl-2-tert-butylglycine

Xhg: N-Methyl-3-tert-butylalanine

Xhh: N-Ethylvaline

Xhi: 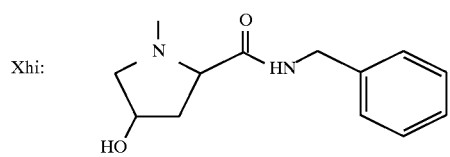

Xhk: 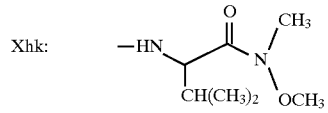

Xhl: 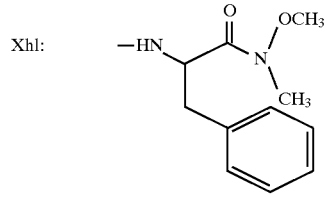

Xhm: 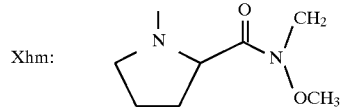

Xhn: N-Ureyl-valine

Xho: N,N-Dimethylphenylalanine

Xhp: N,N-Diethylphenylalanine

Xhq: N,N-Dipropylphenylalanine

Xhr: Hydroxyproline

Xhs: 3-Thienylalanine

Xht: N,N-Dimethyl-3-cyclohexyl-alanine

Xhu: N,N-Diethyl-3-cyclohexyl-alanine

Xhv: N-Methyl-N-isopropyl-tert.-leucine

Xhw: N-Methyl-N-isopropyl-leucine

Xhx: N-Methyl-N-isopropyl-isoleucine

Xhy: N-Methyl-3-cyclohexyl-alanine

Xhz: N-Methyl-phenylalanine

Xia: 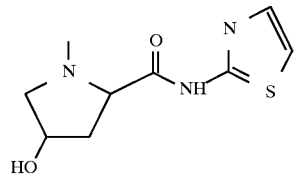

Xib: 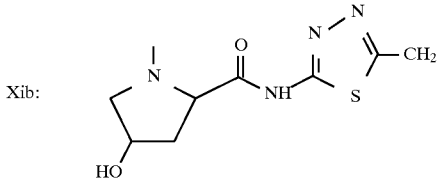

Xic: 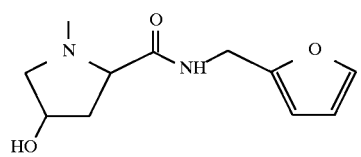

Xid: 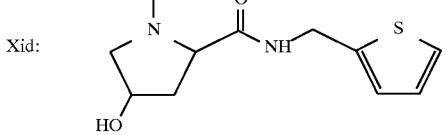

Xhi: 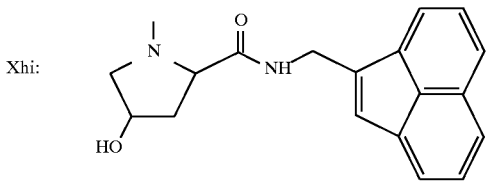

Xif: 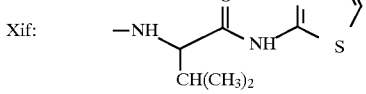

Xig: 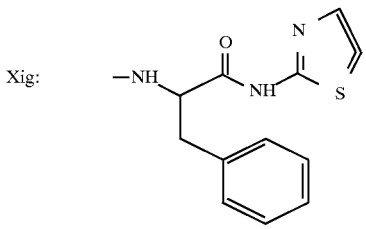

Xih: 2-Cyclohexylglycine

Xii: N-Methyl-2-cyclohexylglycine

| | | |
|---|---|---|
| Xik: | 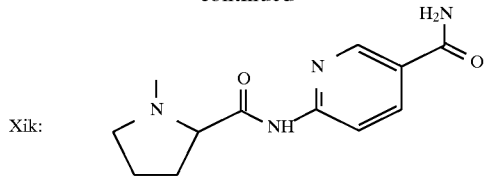 | |
| Xil: | 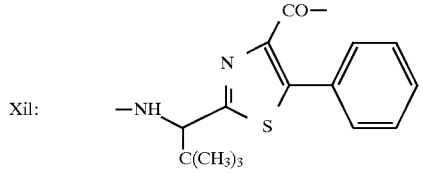 | |
| Xim: | N-Methylaminosulfonyl-valine | |
| Xin: | N-tert.butylaminosulfonyl-valine | |
| Xio: | N-Morpholinosulfonyl-valine | |
| Xip: | N-Benzyloxycarbonyl-valine | |
| Xiq: | N-tert.Butyloxycarbonyl-valine | |
| Xir: | Phenylalanine-methylester | |
| Xis: | Phenylalanine-ethylester | |
| Xit: | Phenylalanine-benzylester | |
| Xiu: | Phenylalanine-tert.butylester | |
| Xiv: | Valine-benzylester | |
| Xiw: | Valine-methylester | |
| Xix: | Valine-ethylester | |
| Xiy: | Valine-tert.butylester | |
| Xiz: | Proline-benzylester | |
| Xka: | Proline-methylester | |
| Xkb: | Proline-ethylester | |
| Xkc: | Proline-tert.butylester | |
| Xkd: | N-Lactyl-valine | |
| Xke: | N-Methylsulfonyl-valine | |
| Xkf: | N-Methyl-N-methylsulfonyl-valine | |
| Xkg: | N-Tosyl-valine | |
| Xkh: | N-Phthalyl-valine | |

| | | |
|---|---|---|
| Xki: | N-Methyl-alanine | |
| Xkj: | D-phenylalanine | |
| Xkk: | 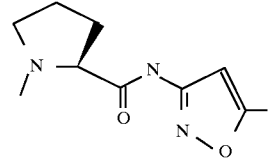 | |
| Xkl: | 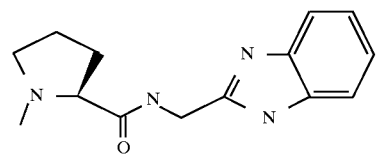 | |
| Xkm: | N-isopropyl-valine | |
| Xkn: | N,N-Dimethyl-2-amino-butyric acid | |
| Xko: | 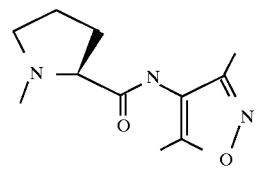 | |
| Xkp: | 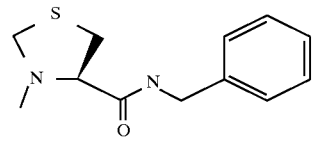 | |
| Xkq: | N-Methyl-N-ethyl-valine | |
| Xkr: | 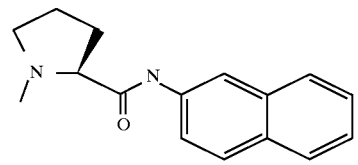 | |
| Xks: | 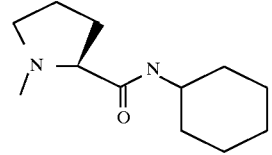 | |
| Xkt: | 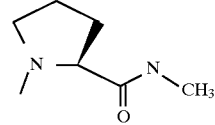 | |
| Xku: | 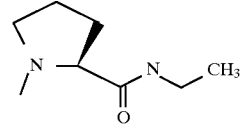 | |

| | |
|---|---|
| Xkv: | *(pyrrolidine-N-methyl, C(=O)-NH-propyl-CH3)* |
| Xkw: | *(pyrrolidine-N-methyl, C(=O)-O-CH(CH3)2 isopropyl ester)* |
| Xkx: | *(pyrrolidine-N-methyl, C(=O)-NH-CH2-cyclohexyl)* |
| Xky: | *(pyrrolidine-N-methyl, C(=O)-NH-indan-2-yl)* |
| Xkz: | *(pyrrolidine-N-methyl, C(=O)-NH-CH2-C6H4-4-CF3)* |
| Xla: | *(pyrrolidine-N-methyl, C(=O)-NH-CH2-C6H4-4-N(CH3)2)* |
| Xlb: | *(pyrrolidine-N-methyl, C(=O)-N(H)-O-CH2-phenyl)* |
| Xlc: | Proline adamantylamide |
| Xld: | *(pyrrolidine-N-methyl, C(=O)-NH-CH2-CF3)* |
| Xle: | *(pyrrolidine-N-methyl, C(=O)-NH-CH2-C6H4-4-COOCH3)* |
| Xlf: | *(pyrrolidine-N-methyl, C(=O)-NH-CH2CH2-OCH3)* |
| Xlg: | *(piperidine-N-methyl, C(=O)-NH-CH2-phenyl)* |
| Xlh: | *(pyrrolidine-N-methyl, C(=O)-NH-cyclopropyl)* |
| Xli: | *(pyrrolidine-N-methyl, C(=O)-NH-CH2CH2-phenyl)* |
| Xlk: | *(pyrrolidine-N-methyl, C(=O)-NH-CH2CH2CH2-phenyl)* |
| Xll: | *(pyrrolidine-N-methyl, C(=O)-NH-CH2CH2CH2-CH3)* |
| Xlm: | *(pyrrolidine-N-methyl, C(=O)-NH-CH2-C(CH3)3 neopentyl)* |
| Xln: | *(pyrrolidine-N-methyl, C(=O)-NH-pyridin-2-yl)* |
| Xlo: | *(pyrrolidine-N-methyl, C(=O)-NH-CH2-CH(CH3)2 isobutyl)* |
| Xlp: | *(pyrrolidine-N-methyl, C(=O)-NH-CH(CH3)-CH(OH)-phenyl)* |

-continued

Xlq: 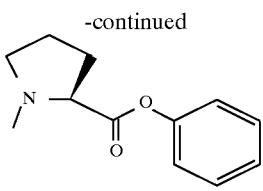

Xlr: 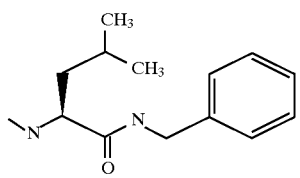

Xls: 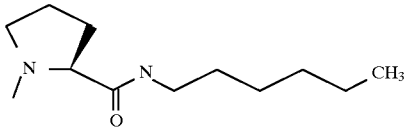

Xlt: 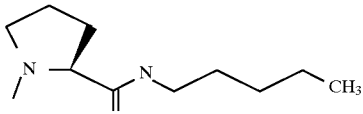

Xlu: 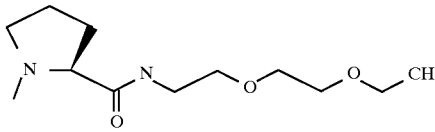

Xlv:   3-naphthylalanyl

Xlx:   3-cyclohexylalanyl

Xma:   2-ethylglycyl

The ending —$NH_2$ has the meaning that the C-terminal amino acid is in its amide form.

Compounds of this invention may be assayed for anti-cancer activity by conventional methods, including for example, the methods described below.

A. In vitro methodology

Cytotoxicity was measured using a standard methodology for adherent cell lines such as the microculture tetrazolium assay (MTT). Details of this assay have been published (Alley, MC et al, Cancer Research 48:589–601, 1988). Exponentially growing cultures of tumor cells such as the HT-29 colon carcinoma or LX-1 lung tumor are used to make microtiter plate cultures. Cells are seeded at 5000–20,000 cells per well in 96-well plates (in 150 μl of media), and grown overnight at 370° C. Test compounds are added, in 10-fold dilutions varying from $10^{-4}$ M to $10^{-10}$ M. Cells are then incubated for 48 hours. To determine the number of viable cells in each well, the MTT dye is added (50 μl of 3 mg/ml solution of 3-(4,5-dimethylthiazol-2-yl) -2,5-diphenyltetrazolium bromide in saline). This mixture is incubated at 370° C. for 5 hours, and then 50 μl of 25% SDS, pH2 is added to each well. After an overnight incubation, the absorbance of each well at 550 nm is read using an ELISA reader. The values for the mean ±SD of data from replicated wells are calculated, using the formula % T/C (% viable cells treated/control).

$$\frac{OD \text{ of treated cells}}{OD \text{ of control cells}} \times 100 = \% \ T/C$$

The concentration of test compound which gives a T/C of 50% growth inhibition was designated as the $IC_{50}$ value. The following results were obtained:

| COMPOUND OF EXAMPLE | $IC_{50}$ [M] |
|---|---|
| 14 | $3 \times 10^{-7}$ |
| 19 | $8 \times 10^{-5}$ |
| 20 | $2 \times 10^{-9}$ |
| 21 | $>10^{-4}$ |
| 23 | $2 \times 10^{-5}$ |
| 25 | $2 \times 10^{-4}$ |
| 26 | $6 \times 10^{-8}$ |
| 27 | $5 \times 10^{-6}$ |
| 29 | $>10^{-4}$ |
| 30 | $>10^{-4}$ |
| 52 | $5 \times 10^{-5}$ |
| 55 | $2 \times 10^{-6}$ |
| 56 | $4 \times 10^{-7}$ |
| 57 | $4 \times 10^{-6}$ |
| 58 | $10^{-5}$ |
| 62 | $3 \times 10^{-5}$ |
| 65 | $4 \times 10^{-7}$ |
| 66 | $2 \times 10^{-7}$ |
| 68 | $6 \times 10^{-7}$ |
| 73 | $2 \times 10^{-5}$ |
| 86 | $10^{-7}$ |
| 87 | $4 \times 10^{-8}$ |
| 88 | $2 \times 10^{-9}$ |
| 93 | $5 \times 10^{-9}$ |
| 94 | $>10^{-4}$ |
| 95 | $5 \times 10^{-7}$ |
| 102 | $10^{-4}$ |
| 146 | $2 \times 10^{-5}$ |
| 157 | $2 \times 10^{-4}$ |
| 204 | $4 \times 10^{-9}$ |
| 214 | $10^{-9}$ |
| 215 | $3 \times 10^{-9}$ |
| 227 | $10^{-8}$ |
| 230 | $10^{-9}$ |
| 233 | $10^{-9}$ |
| 234 | $3 \times 10^{-10}$ |
| 238 | $6 \times 10^{-7}$ |
| 239 | $6 \times 10^{-8}$ |
| 241 | $>10^{-6}$ |
| 246 | $10^{-8}$ |
| 247 | $>10^{-4}$ |
| 284 | $6 \times 10^{-7}$ |
| 339 | $>10^{-6}$ |
| 340 | $>10^{-6}$ |
| 347 | $3 \times 10^{-7}$ |
| 349 | $6 \times 10^{-7}$ |
| 351 | $7 \times 10^{-8}$ |
| 352 | $2 \times 10^{-8}$ |
| 357 | $8 \times 10^{-9}$ |
| 361 | $>10^{-6}$ |
| 400 | $2 \times 10^{-4}$ |
| 404 | $4 \times 10^{-7}$ |
| 405 | $3 \times 10^{-7}$ |
| 411 | $>10^{-5}$ |
| 417 | $2 \times 10^{-5}$ |
| 521 | $>10^{-4}$ |

Further compounds of this invention were assayed for anti-cancer activity by the crystal violet assay for cytotoxicity.

This assay was performed according to the method described by Flick H. and Gifford, G. E., J. Immunol. Meth. 68, 167–175 (1984). Proteins of surviving adherent cells are stained after exposure to a cytotoxic drug and quantitated calorimetrically. Test cells (CX-I; colon carcinoma, human) were plated in 96 flat bottom microtiter plates at a density of 2–3×$10^3$ cells/well and incubated under standard culture conditions (RPMI 1640 with 10% fetal calf serum and 1% non-essential amino acids) at 37° C. and 5% $CO_2$ for one day. The cells were then exposed to several concentrations of the test compound. Controls were incubated in medium alone. After a further incubation period of 72 h, the culture medium was removed by flicking and 50 µl of a crystal violet staining solution were added to each well. After a staining period of 20 min, the staining solution was removed and the plates were washed vigorously with water until all unbound dye was removed. The remaining insoluble dye crystals were dissolved by adding 100 µl of a solution containing 50% ethanol and 0.1% acetic acid to each well. The absorbance of each well was determined using an ELISA microtiter plate reader at 540 nm (Titertec Multiscan, Flow Lab., Meckenheim).

The concentration of test compound which gives a T/C of 50% growth inhibition was designated as the $IC_{50}$. The following results were obtained:

| COMPOUND OF EXAMPLE | $IC_{50}$ [M] |
|---|---|
| 1 | $9 \times 10^{-8}$ |
| 2 | $4 \times 10^{-8}$ |
| 3 | $6 \times 10^{-7}$ |
| 8 | $5 \times 10^{-6}$ |
| 9 | $4 \times 10^{-8}$ |
| 10 | $6 \times 10^{-8}$ |
| 13 | $2 \times 10^{-7}$ |
| 16 | $9 \times 10^{-7}$ |
| 28 | $3 \times 10^{-8}$ |
| 31 | $10^{-5}$ |
| 33 | $2 \times 10^{-5}$ |
| 34 | $4 \times 10^{-8}$ |
| 36 | $2 \times 10^{-5}$ |
| 37 | $4 \times 10^{-7}$ |
| 38 | $3 \times 10^{-10}$ |
| 48 | $4 \times 10^{-7}$ |
| 50 | $2 \times 10^{-7}$ |
| 51 | $5 \times 10^{-7}$ |
| 59 | $8 \times 10^{-6}$ |
| 101 | $2 \times 10^{-4}$ |
| 406 | $4 \times 10^{-7}$ |
| 407 | $9 \times 10^{-7}$ |
| 408 | $2 \times 10^{-6}$ |
| 538 | $10^{-10}$ |

B. In vivo methodology

Compounds of this invention were further tested in preclinical assay for in vivo activity which is indicative of clinical utility. Such assays were conducted with nude mice into which tumor tissue, preferably of human origin, had been transplanted (xenografted), as is well known in this field. Test compounds were evaluated for their anti-tumor efficacy following administration to the xenograft-bearing mice.

More specifically, human breast tumors (MX-1) which had been grown in athymic nude mice were transplanted into new recipient mice, using tumor fragments which were about 50 mg in size. The day of transplantation was designated as day 0. Six to ten days later, mice were treated with the test compounds given as an intravenous injection, in groups of 5–10 mice at each dose. Compounds were given every other day, for 3 weeks, at doses from 1–100 mg/kg body weight. Tumor diameters and body weights were measured twice weekly. Tumor volumes were calculated using the diameters measured with Vernier calipers, and the formula (length×width$^2$)/2=mm$^3$ of tumor volume Mean tumor volumes are calculated for each treatment group, and T/C values determined for each group relative to the untreated control tumors.

Figure 2:
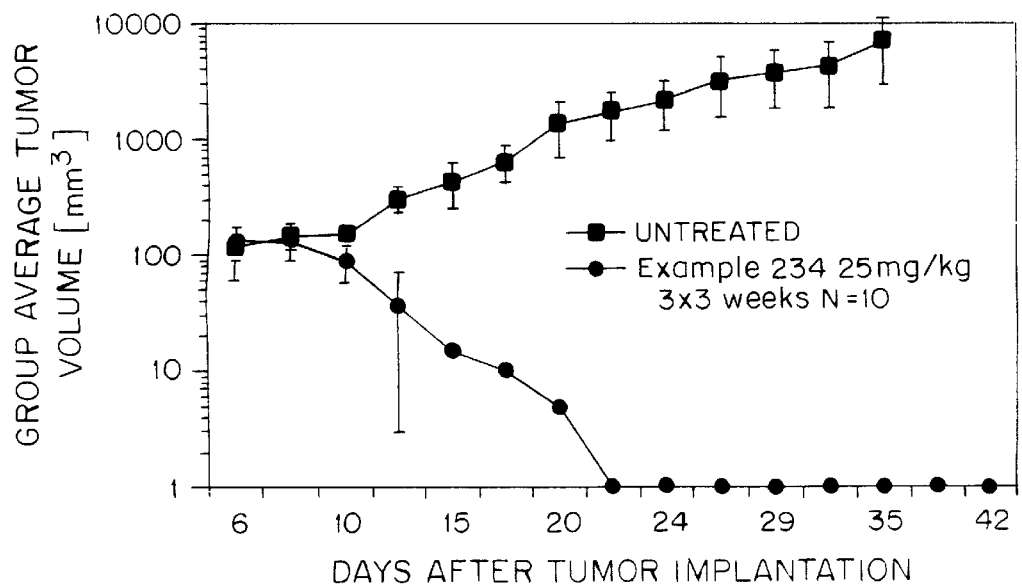

In the second example as shown in FIG. 2., mice were treated with compound example #234, at 25 mg/kg 3 times a week for 3 weeks. All tumors in the treated group disappeared, while the control tumors grew so large the mice were sacrificed. No regrowth of the tumor was observed in the treated mice.

Representative Compounds Tested in Vivo

Additional compounds were also tested in the MX-1 model as described above. Compounds were administered i.v. Compounds which had good activity in the MX-1 model were also tested in additional in vivo models.

| EXAMPLE | ACTIVITY* | COMMENTS |
|---|---|---|
| 2 | + | tumor growth delay |
| 37 | ++ | regressions, active in other models |
| 38 | +++ | cures, active in other models |
| 50 | +++ | cures, active in other models |
| 230 | ++ | regressions |
| 595 | +++ | cures, active in other models |
| 610 | ++ | regressions |
| 611 | ++ | regressions |
| 627 | +++ | cures, active in other models |
| 629 | +++ | cures, active in other models |

[*]:
+ tumor growth delay
++ regressions
+++ cures
other models P388 leukemia, OVCAR ovarian carcinoma, LOX human melanoma These data show that the new compounds possess good tumor inhibiting properties.

We claim:
1. A peptide of the formula I

$$R^1R^2N-CHX-CO-A-B-D-(E)_s-(F)_t-(G)_u-K \qquad I$$

where
$R^1$ is alkoxy; alkyl; cycloalkyl; alkylsulfonyl; fluoroalkyl; aminosulfonyl, which may be substituted by alkyl; hydroxy; or benzyl, which may be substituted by up to three substituents independently selected from alkyl, alkoxy, nitro, halogen and $CF_3$;
$R^2$ is hydrogen, alkyl; fluoroalkyl; or cycloalkyl;
$R^1-N-R^2$ together may form a 5-or 6-membered heterocycle which may be unsubstituted or substituted with one or more substituents independently selected from alkyl, $N(CH_3)_2$, nitro, $CONH_2$, and COOEt;
A is a valyl, isoleucyl, leucyl, allo-isoleucyl, 2,2-dimethylglycyl, 3-tert-butylalanyl, 2-tert-butylglycyl, 3-cyclohexylalanyl, 2-ethylglycyl, 2-cyclohexylglycyl, norleucyl, 2-cyclopropylglycyl, 2-cyclopentylglycyl or norvalyl residue;
B is an N-alkyl-valyl, -norvalyl, -leucyl, -isoleucyl, -2-tert-butylglycyl, -3-tert-butylalanyl, -2-ethylglycyl, -norleucyl, -2-cyclopropylglycyl, -2-cyclopentylglycyl, or -2-cyclohexylglycyl residue;
D is a prolyl, homo-prolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;
E is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydroisoquinolyl-2-carbonyl, 3-thiazolylalanyl, 3-thienylalanyl, histidyl, 1-aminoindyl-1-carbonyl, 3-pyridylalanyl, 2-cyclohexylglycyl norvalyl, norleucyl, tryptophanyl, neopentylglycyl, β-alanyl and 3-naphthylalanyl residues;

X is hydrogen; alkyl; cycloalkyl; —CH$_2$-cyclohexyl or arylalkyl;

s, t, and u are independently 0 or 1; and

K is hydroxy, alkoxy, benzyloxy, phenyloxy or an amino moiety of the formula R$^5$—N—R$^6$, wherein R$^5$ is selected from the group consisting of: hydrogen; hydroxy; alkoxy; substituted or unsubstituted benzyloxy; substituted or unsubstituted phenoxy; fluorine-substituted or unsubstituted, linear or branched alkyl; cycloalkyl; and substituted and unsubstituted benzyl; and R$^6$ is selected from the group consisting of: hydrogen; fluorine-substituted or unsubstituted, linear or branched alkyl; aryl; cycloalkylalkyl; arylalkyl; heteroarylalkyl; heteroaryl; (CH$_2$CH$_2$O)$_y$R, wherein y is 1 to 5 and R is an alkyl group; —CHR$^7$-5-membered heteroaryl, wherein the heteroaryl group is substituted or unsubstituted and R$^7$ is hydrogen, linear or branched C$_{1-4}$-C$_5$-alkyl, or benzyl, or R$^5$ and R$^7$ together form a group —(CH$_2$)$_3$- or —(CH$_2$)$_4$-; and NR$^a$R$^b$, wherein R$^a$ is hydrogen or methyl and R$^b$ is a substituted or unsubstituted phenyl or benzyl group; or wherein R$^5$, R$^6$ and N together form a heteroaryl- or substituted heteroaryl-substituted 5- or 6-membered ring; or wherein R$^5$, R$^6$ and N together form a ring system selected from the group consisting of:

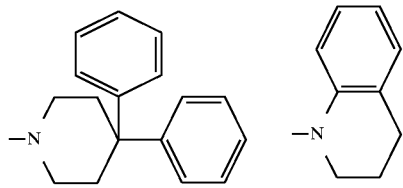

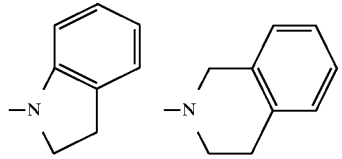

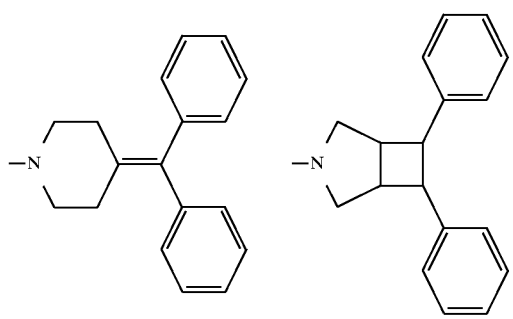

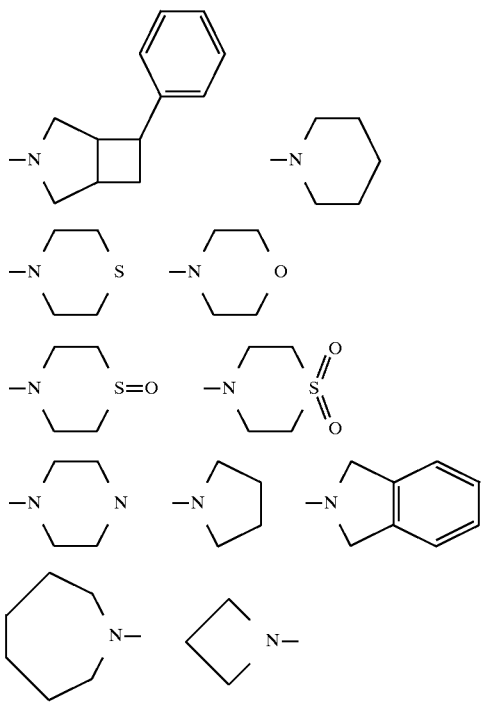

or a salt thereof with a physiologically tolerated acid.

2. A compound of formula I as defined in claim 1 wherein R$^1$—N—R$^2$ together form a 5- or 6-membered heterocycle which may be unsubstituted or substituted with one or more substituents which may independently be selected from alkyl, N(CH$_3$)$_2$, nitro, oxo, CONH$_2$ and COOEt.

3. The compound of claim 1 wherein K is an amino moiety of the formula R$^5$—N—R$^6$ wherein R$_5$ is hydrogen; hydroxy; C$_{1-7}$ alkoxy; C$_{3-7}$-cycloalkyl; benzyloxy, optionally having up to three substituents independently selected from the group consisting of CF$_3$; nitro; C$_{1-7}$ alkylsulfonyl; C$_{1-4}$ alkoxy; phenoxy; benzyloxy; halogen; C$_{1-4}$-alkyl; cyano; hydroxy; N(CH)$_3$)$_2$; COOMe; COOEt; COOiPr and COONH$_2$;

phenyloxy, optionally having up to three substituents independently selected from the group consisting of CF$_3$; nitro; C$_{1-7}$ alkylsulfonyl; C$_{1-4}$ alkoxy; phenoxy; benzyloxy; halogen; C$_{1-4}$-alkyl; cyano; hydroxy; N(CH$_3$)$_2$; COOMe; COOEt; COOiPr; and COONH$_2$;

C$_{1-7}$-alkyl, optionally substituted by one or more fluorine atoms; or benzyl, optionally having up to three substituents independently selected from the group consisting of CF$_3$; nitro; C$_{1-7}$ alkylsulfonyl; C$_{1-4}$ alkoxy; phenoxy; benzyloxy; halogen; C$_{1-4}$-alkyl; cyano; hydroxy; N(CH$_3$); COOMe; COOEt; COOiPr and COONH$_2$;

R$^6$ is hydrogen; norephedryl; norpseudoephedryl; quinolyl; pyrazyl; —CH$_2$-benzimidazolyl; adamantyl; —CH$_2$-adamantyl; alpha-methyl-benzyl; alpha-dimethylbenzyl;

C$_{1-12}$-alkyl, optionally substituted by one or more fluorine atoms;

—(CH$_2$)$_v$-C$_{3-7}$-cycloalkyl, wherein v=0,1,2, or 3;

—(CH$_2$)$_v$-phenyl, wherein v=0,1,2, or 3, optionally having up to three substituents independently selected from the group consisting of CF$_3$; nitro;

$C_{1-7}$ alkylsulfonyl; $C_{1-4}$ alkoxy; phenoxy; benzyloxy; halogen; $C_{1-4}$-alkyl which may form a cyclic system; cyano; hydroxy; $N(CH_3)_2$; COOMe; COOEt; COOiPr and COONH$_2$;

—(CH$_2$)$_m$-naphthyl, wherein m=0 or 1, optionally having up to three substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxyl; $N(CH_3)_2$; COOMe; COOEt; COOiPr; or COONH$_2$; or —(CH$_2$)$_w$-benzhydryl, wherein w=0, 1, or 2, optionally having up to three substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; $N(CH_3)_2$; COOMe; COOEt; COOiPr and COONH$_2$;

biphenyl, optionally having up to three substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; $N(CH_3)_2$; COOMe; COOEt; COOiPr and COONH$_2$;

pyridyl, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

picolyl, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

—CH$_2$—CH$_2$-pyridyl, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

benzothiazolyl, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

benzopyrazolyl, optionally having up to two substituents independently selected from the group consisting of CF$_3$; nitro; $C_{1-7}$ alkylsulfonyl; $C_{1-4}$ alkoxy; halogen; $C_{1-4}$- alkyl which may form a cyclic system; cyano; hydroxy; COOMe; COOEt; COOiPr and COONH$_2$;

benzoxazolyl, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

—(CH$_2$)$_m$-fluorenyl, wherein m is 0 or 1, optionally having up to three substituents independently selected from the group consisting of CF$_3$; nitro; $C_{1-7}$ alkylsulfonyl; $C_{1-4}$ alkoxy; halogen; $C_{,1-4}$-alkyl which may form a cyclic system; cyano; hydroxy; $N(CH_3)_2$; COOMe; COOEt; COOiPr and COONH$_2$;

pyrimidyl, optionally having up to three substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; $N(CH_3)_2$; COOMe; COOEt; COOiPr and COONH$_2$;

—(CH$_2$)$_m$-indanyl, wherein m=0 or 1, optionally having up to three substituents independently selected from the group consisting of CF$_3$; nitro; $C_{1-7}$ alkylsulfonyl; $C_{1-4}$ alkoxy; halogen; $C_{1-4}$-alkyl, which may form a cyclic system; cyano; hydroxy; $N(CH_3)_2$; COOMe; COOEt; COOiPr and COONH$_2$;

—(CH$_2$CH$_2$O)$_y$—CH$_3$, wherein y=0,1,2,3,4, or 5;

—(CH$_2$CH$_2$O)$_y$—CH$_2$CH$_3$, wherein y=0, 1,2,3,4, or 5;

—NH-C$_6$H$_5$, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

—NCH$_3$-C$_6$H$_5$, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

—NH—CH$_2$C$_6$H$_5$, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

—NCH$_3$—CH$_2$C$_6$H$_5$, optionally having up to two substituents independently selected from the group consisting of CF$_3$; nitro; $C_{1-7}$ alkylsulfonyl; $C_{1-4}$ alkoxy; halogen; $C_{1-4}$-alkyl which may form a cyclic system; cyano; hydroxy; COOMe; COOEt; COOiPr and COONH$_2$;

5-membered heteroaryl, optionally having up to three substituents independently selected from the group consisting of CF$_3$; nitro; $C_{1-7}$ alkylsulfonyl; $C_{1-4}$ alkoxy; thiomethyl; thioethyl; picolyl; acetyl; $C_{3-6}$-cycloalkyl; thiophenyl; —CH$_2$—COOEt; $C_{3-4}$-alkylene group forming a bicyclic system with the heterocycle; phenyl; phenyl substituted by up to three substituents which may independently be nitro, CF$_3$, CN, halogen, or $C_{1-4}$-alkyl; benzyl; or benzyl substituted by up to three substituents which may independently be nitro, CF$_3$, halogen, $C_{1-4}$-alkyl, $C_{1-7}$-alkylsulfonyl, cyano, hydroxy or $C_{1-4}$-dialkylamino; or —CHR$^7$-5-membered heteroaryl, wherein R$^7$ is hydrogen; linear or branched $C_{1-5}$ alkyl or benzyl; or R$^7$ and R$^5$ together form a group —(CH$_2$)$_3$- or —(CH$_2$)$_4$-, optionally having up to two substituents which may independently be CF$_3$; nitro; cyano; halogen; COOMe; COOEt; COOiPr; CONH$_2$; $C_{1-4}$-alkyl; $C_{1-4}$-alkoxy; phenyl; benzyl; naphthyl or $C_{1-7}$-alkylsulfonyl.

4. A compound of formula I as defined in claim 1 wherein K is R$^5$—N—R$^6$ which together may form structures selected from the group consisting of

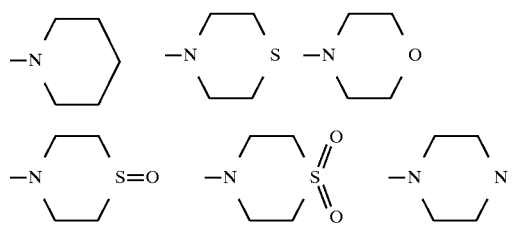

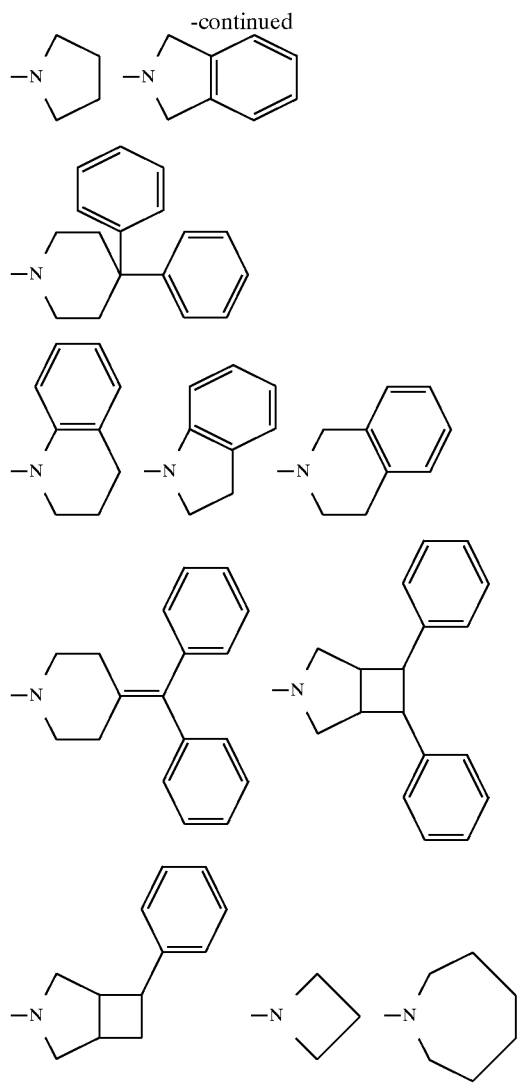

which may be unsubstituted or substituted with one or more substituents independently selected from the group consisting of $CF_3$, nitro, halogen, oxo, cyano, formyl, N,N-dimethylamino, $C_{1-6}$-alkyl, $C_{3-6}$-cycloalkyl, $C_{3-4}$-alkylene group forming a bicyclic system with the heterocycle, $C_{1-4}$-alkoxy, phenoxy, benzoxy, naphthyl, pyrimidyl, COOEt, pyrrolidinyl, piperidinyl, thienyl, pyrrolyl, $CH_2$-CO-NCH$(CH_3)_2$, —$CH_2$—CO-N$(CH_2)_4$, —$CH_2$-CO-N$(CH_2)_4$O, benzyl (which may be substituted by up to three substituents independently selected from the group consisting of nitro, halogen, $CF_3$, thiomethyl or the corresponding sulfoxide or sulfone, thioethyl or the corresponding sulfoxide or sulfone, $C_{1-4}$-alkyl, and $C_{1-4}$-alkoxy).

5. A compound of formula I as defined in claim 1 wherein s, t and u are 1 and K is a hydroxy, alkoxy, phenoxy or benzyloxy moiety.

6. A compound of formula I as defined in claim 1 wherein s and t are 1, u is 0 and K is a hydroxy, alkoxy, phenoxy or benzyloxy moiety.

7. A compound of formula I as defined in claim 1 wherein s is 1, t and u are 0 and K is a hydroxy, alkoxy, phenoxy or benzyloxy moiety.

8. A compound of formula I as defined in claim 1 wherein K is an amino moiety of the formula $R^5$—N—$R^6$.

9. A pharmaceutical composition comprising a pharmaceutically acceptable carrier and a therapeutically effective amount of a compound of formula I as defined in claim 1.

10. A method of treating a tumor in a mammal comprising administering to a mammal bearing such a tumor, a tumor-inhibiting amount of a compound of formula I as defined in claim 1.

* * * * *